(12) United States Patent
Eckhouse et al.

(10) Patent No.: US 9,844,381 B2
(45) Date of Patent: Dec. 19, 2017

(54) DEVICES AND METHODS FOR ASSISTING MEDICAL TREATMENTS

(71) Applicants: RAPID MEDICAL LTD., Yokneam (IL); Ronen Eckhouse, Shimshit (IL); Yuri Sudin, Modin (IL); Aharon Friedman, Haifa (IL); Shimon Eckhouse, Haifa (IL)

(72) Inventors: Ronen Eckhouse, Shimshit (IL); Yuri Sudin, Modin (IL); Aharon Friedman, Haifa (IL); Shimon Eckhouse, Haifa (IL)

(73) Assignee: RAPID MEDICAL LTD., Yokneam (IL)

( * ) Notice: Subject to any disclaimer, the term of this patent is extended or adjusted under 35 U.S.C. 154(b) by 96 days.

(21) Appl. No.: 14/650,038

(22) PCT Filed: Dec. 4, 2013

(86) PCT No.: PCT/IB2013/003161
§ 371 (c)(1),
(2) Date: Jun. 5, 2015

(87) PCT Pub. No.: WO2014/087245
PCT Pub. Date: Jun. 12, 2014

(65) Prior Publication Data
US 2015/0327866 A1 Nov. 19, 2015

Related U.S. Application Data

(60) Provisional application No. 61/733,755, filed on Dec. 5, 2012.

(30) Foreign Application Priority Data

Jan. 3, 2013 (WO) .................. PCT/IB2013/000359

(51) Int. Cl.
*A61B 17/12* (2006.01)
*A61F 2/82* (2013.01)
(Continued)

(52) U.S. Cl.
CPC .... *A61B 17/12113* (2013.01); *A61B 17/1214* (2013.01); *A61B 17/12109* (2013.01);
(Continued)

(58) Field of Classification Search
CPC ........ A61B 17/12022; A61B 17/12099; A61B 17/12109; A61B 17/12113;
(Continued)

(56) References Cited

U.S. PATENT DOCUMENTS 7,306,618 B2 * 12/2007 Demond .................... A61F 2/01
604/164.05
7,645,296 B2 * 1/2010 Theron .............. A61B 17/1204
623/1.11

(Continued)

FOREIGN PATENT DOCUMENTS

CN 101687067 A 3/2010
CN 202313575 U 7/2012
(Continued)

OTHER PUBLICATIONS

International Search Report mailed Nov. 11, 2014 for PCT/IB2013/003161, corresponding to U.S. Appl. No. 14/650,038 (7 pages).
(Continued)

*Primary Examiner* — Ryan J Severson
(74) *Attorney, Agent, or Firm* — Finnegan, Henderson, Farabow, Garrett & Dunner, L.L.P.

(57) ABSTRACT

A treatment device (500) is provided including a shaft (507), an expandable member, a first elongated control member (508) and a second elongated control member (502). The expandable member can further include at least a first (Continued)

controllable portion (504) and a second controllable portion (503), where the expandable member, including the first controllable portion and the second controllable portion, is configured to transition between at least a partially retracted configuration and an expanded configuration under control of at least the first elongated control member (508). Further still, the first controllable portion can be configured to transition between at least a partially retracted configuration and an expanded configuration, while the second controllable portion (503) is configured to remain substantially unchanged, under control of at least the second elongated control member (502).

28 Claims, 26 Drawing Sheets

(51) Int. Cl.
  *A61F 2/01* (2006.01)
  *A61F 2/844* (2013.01)
  *A61B 17/221* (2006.01)
(52) U.S. Cl.
  CPC .. *A61B 17/12118* (2013.01); *A61B 17/12136* (2013.01); *A61F 2/01* (2013.01); *A61F 2/013* (2013.01); *A61F 2/82* (2013.01); *A61F 2/844* (2013.01); *A61B 2017/2212* (2013.01); *A61F 2002/011* (2013.01); *A61F 2002/016* (2013.01); *A61F 2002/823* (2013.01); *A61F 2230/0069* (2013.01); *A61F 2250/0017* (2013.01)
(58) Field of Classification Search
  CPC ........ A61B 17/12118; A61B 17/12122; A61B 17/12131; A61B 17/1214; A61B 17/12163; A61B 17/12168; A61B 2017/1205; A61F 2/013; A61F 2002/016
  See application file for complete search history.

(56) References Cited

U.S. PATENT DOCUMENTS

| | | | | |
|---|---|---|---|---|
| 8,758,364 | B2* | 6/2014 | Eckhouse | A61B 17/221 606/127 |
| 8,864,792 | B2* | 10/2014 | Eckhouse | A61B 17/221 606/200 |
| 9,005,237 | B2* | 4/2015 | Eckhouse | A61B 17/221 606/200 |
| 9,034,008 | B2* | 5/2015 | Eckhouse | A61B 17/221 606/200 |
| 9,301,769 | B2* | 4/2016 | Brady | |
| 2002/0161393 | A1* | 10/2002 | Demond | A61F 2/01 606/200 |
| 2004/0138692 | A1* | 7/2004 | Phung | A61B 17/221 606/200 |
| 2005/0197688 | A1* | 9/2005 | Theron | A61B 17/1204 623/1.11 |
| 2006/0229638 | A1* | 10/2006 | Abrams | A61B 17/221 606/113 |
| 2008/0208230 | A1 | 8/2008 | Chin et al. | |
| 2011/0152920 | A1* | 6/2011 | Eckhouse | A61B 17/221 606/200 |
| 2011/0202088 | A1* | 8/2011 | Eckhouse | A61B 17/221 606/200 |
| 2012/0041449 | A1* | 2/2012 | Eckhouse | A61B 17/221 606/127 |
| 2012/0041474 | A1* | 2/2012 | Eckhouse | A61B 17/221 606/200 |
| 2012/0165858 | A1* | 6/2012 | Eckhouse | A61B 17/221 606/200 |
| 2012/0165859 | A1* | 6/2012 | Eckhouse | A61B 17/221 606/200 |
| 2013/0325055 | A1* | 12/2013 | Eckhouse | A61B 17/221 606/200 |
| 2013/0325056 | A1* | 12/2013 | Eckhouse | A61B 17/221 606/200 |
| 2013/0345739 | A1* | 12/2013 | Brady | A61B 17/221 606/200 |
| 2014/0243885 | A1* | 8/2014 | Eckhouse | A61F 2/01 606/200 |
| 2014/0343663 | A1 | 11/2014 | Suden et al. | |
| 2015/0327866 | A1* | 11/2015 | Eckhouse | A61B 17/12113 623/1.15 |

FOREIGN PATENT DOCUMENTS

| | | |
|---|---|---|
| EP | 0533321 A2 | 3/1993 |
| EP | 1 574 169 A2 | 9/2005 |
| JP | H05-192407 A | 8/1993 |
| JP | 2008-100078 A | 5/2008 |
| JP | 2008-534133 A | 8/2008 |
| WO | WO 99/16363 | 4/1999 |
| WO | WO 2006/104881 A2 | 10/2006 |
| WO | WO 2008/108839 A2 | 8/2008 |

OTHER PUBLICATIONS

International Written Opinion dated Jun. 9, 2015 for PCT/IB2013/003161, corresponding to U.S. Appl. No. 14/650,038 (8 pages).

Chinese Office Action dated Oct. 31, 2016 and Search Report for Chinese Patent Appl. No. 201380059082.0, corresponding to U.S. Appl. No. 14/650,038 (16 pages total).

Australian Examination Report for Australian Patent Appl. No. 2013353760 dated Mar. 29, 2017, corresponding to U.S. Appl. No. 14/650,038 (3 pages).

Office Action from Japanese Patent Office for Japanese Patent Appl. No. 2015-546104 (corresponding to U.S. Appl. No. 14/650,038) dated Jul. 28, 2017 and English language translation (6 pages total).

\* cited by examiner

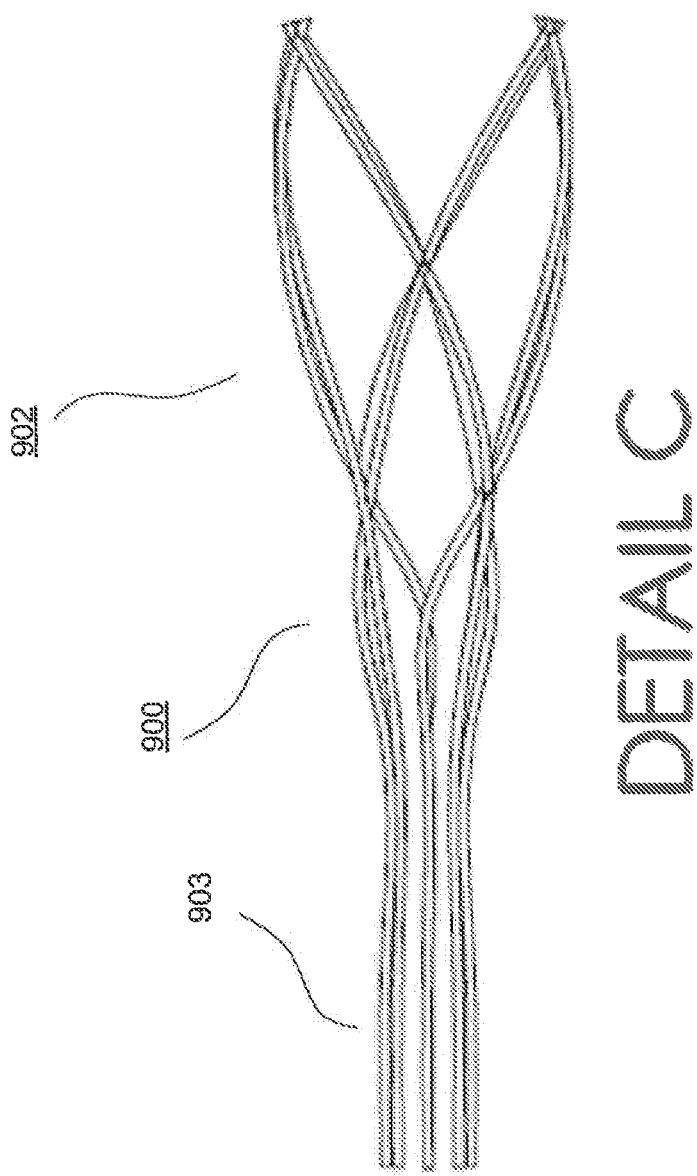

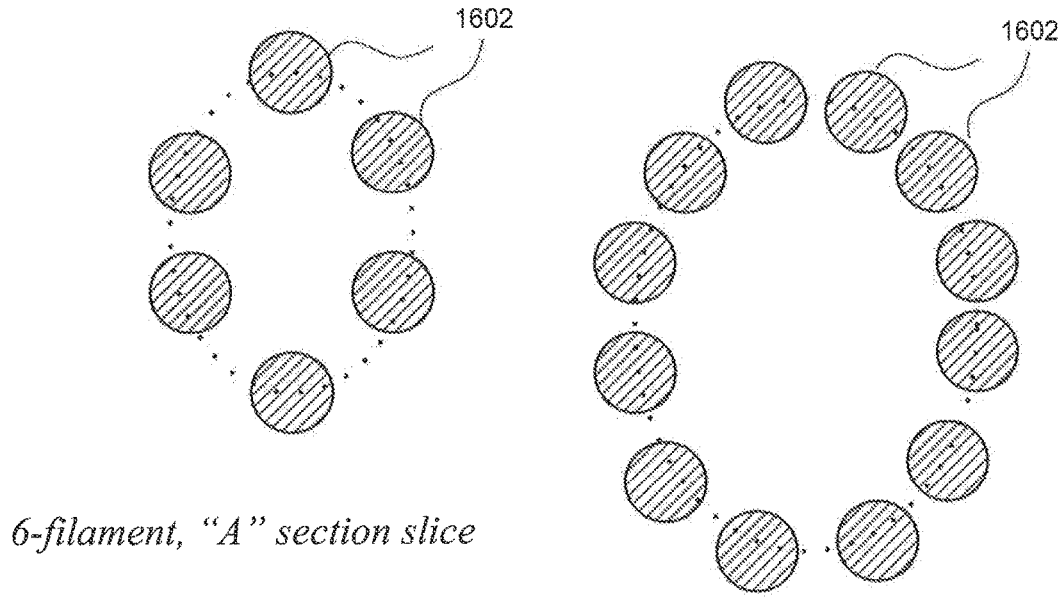
*6-filament, "A" section slice*
FIG. 16A
*12-filament, "A" section slice*
FIG. 16B
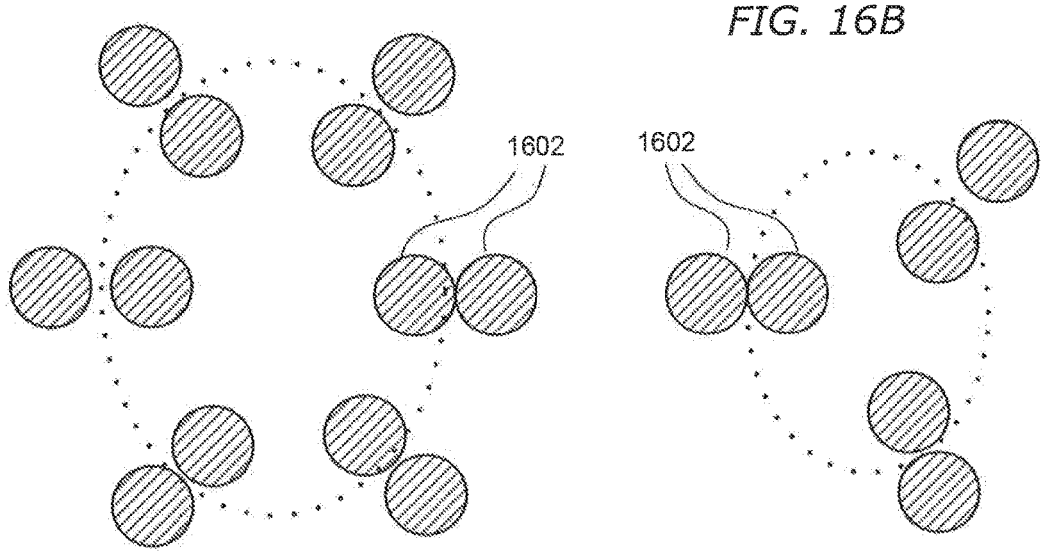
*12-filament, "B" section slice*
FIG. 16D
*6-filament, "B" section slice*
FIG. 16C

DEVICES AND METHODS FOR ASSISTING MEDICAL TREATMENTS

PRIORITY

This application claims the benefit of priority from U.S. Provisional Application No. 61/733,755 filed Dec. 5, 2012, the disclosure of which is herein incorporated by reference in its entirety.

BACKGROUND

An aneurysm is an abnormal local dilatation in the wall of a blood vessel, usually an artery, due to a defect, disease, or injury. One type of aneurysm is an intracranial aneurysm (IA). IAs have a risk of rupturing, which can result in a subarachnoid hemorrhage, a serious medical condition, often leading to severe neurological deficit or death.

A treatment goal of IAs is the prevention of rupture. Treatment methods can include two intervention options: clipping of the aneurysm neck and endovascular methods such as coiling and flow diversion. Traditionally, surgical clipping has been the treatment modality of choice for both ruptured and un-ruptured IAs; however, since the introduction of controlled detachable coils (GDC) for packing of aneurysms, endovascular aneurysm therapy has become an acceptable alternative to conventional neurosurgical treatment.

The technique of standard coil embolization can be limited by the shape of some of these aneurysms. For example, wide-necked aneurysms can be difficult to treat because of their unfavorable geometry, which can reduce the possibility of achieving dense packing and elimination of the aneurysm from circulation. One risk is the possibility of coil herniation through the broad neck into the parent vessel. This can cause thromboembolic events, which can be the most frequent and serious complications associated with endovascular treatment of intracranial aneurysms.

Various adjunctive techniques have been developed for the treatment of large, wide-neck and other complicated aneurysms. One technique is balloon-assisted treatment, in which a balloon is temporarily inflated across the aneurysm neck during coil insertion. In recent years, stents for intracranial use have become available, first as balloon-mounted stents and later as self-expandable stents with an open-cell or closed-cell design.

SUMMARY

In an aspect, a treatment device consistent with this disclosure can include a shaft, including a distal end, and an expandable member—including a proximal end and a distal end. The treatment device can also include a first elongated control member and a second elongated control member. In an aspect, the proximal end of the expandable member can be coupled to the distal end of the shaft. Moreover, the expandable member can further include at least a first controllable portion and a second controllable portion, where the expandable member, including the first controllable portion and the second controllable portion, is configured to transition between at least a partially retracted configuration and an expanded configuration under control of at least the first elongated control member. Further still, the first controllable portion can be configured to transition between at least a partially retracted configuration and an expanded configuration, while the second controllable portion is configured to remain substantially unchanged, under control of at least the second elongated control member.

In a further aspect consistent with this disclosure, a method of treatment can include deploying a treatment device into a blood vessel, transitioning an expandable member from at least a partially retracted configuration to an expanded configuration by exerting a force on a first elongated control member in a first direction, and transitioning a first controllable portion of the expandable member from at least an expanded configuration to a partially retracted configuration, while keeping a second controllable portion substantially unchanged by exerting a force on a second elongated control member in a second direction. In an aspect, the treatment device can include a shaft having a distal end and an expandable member, where the expandable member can be coupled to the distal end of the shaft. Further, in an aspect, the expandable member can include the first controllable portion and the second controllable portion. Further still, the first direction and the second direction can be selected from a group of directions including: a proximal direction and a distal direction.

BRIEF DESCRIPTION OF THE DRAWINGS

FIG. 10C depicts a detail of the embodiment of FIG. 9 near a proximal end of the expandable member;

FIG. 16A-D depicts filament arrangements for 6-filament and 12-filament devices along selected planes;

DESCRIPTION OF EXEMPLARY EMBODIMENTS

Embodiments of the present disclosure provide devices and methods for assisting medical treatments (for example, and without limitation, assisting endovascular treatment of aneurysm and biliary tract treatment). In addition, embodiments of the described devices can also be used as a temporary scaffold for vessel protection during surgery, to remove clots from blood vessels and cross occluded sections of vessels. Further embodiments of described devices can also be used to treat vessel vasospasm and to expand other endovascular devices.

Figure 1:
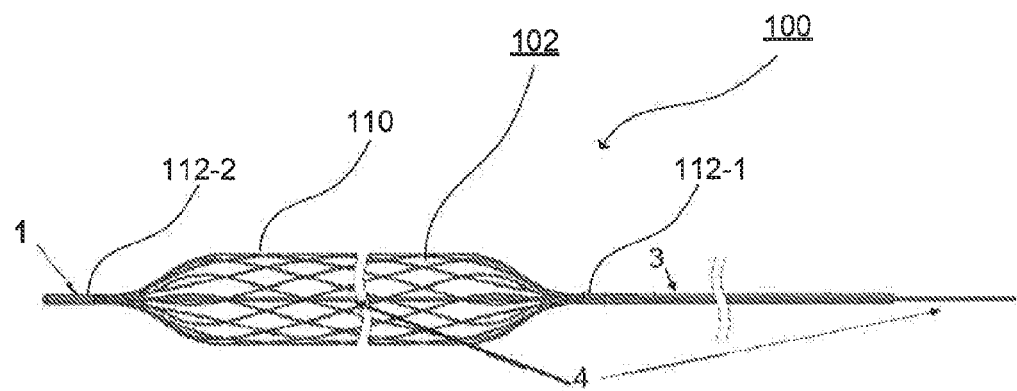
FIG. 1 is a perspective view of an embodiment of a device consistent with the disclosure exhibiting a substantially uniform shape.
Figure 2:
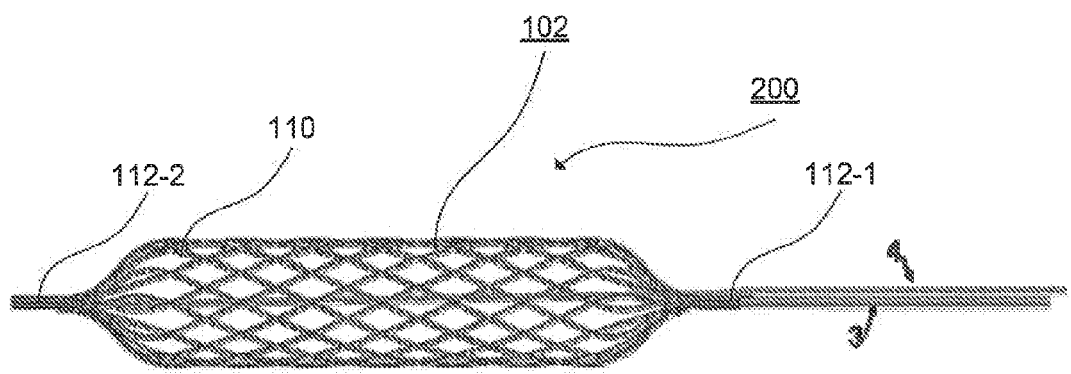
FIG. 2 is a perspective view of further embodiment consistent with the disclosure exhibiting a substantially uniform shape.

A device 100 consistent with the present disclosure is depicted in FIG. 1. The device 100 can include an expandable member 110 that can be mounted on or otherwise coupled to a shaft 3. As used herein, an expandable member can be any known mechanically expandable device, and can include a mesh, a balloon, or any other mechanical structure. Moreover, the expandable member can be made of any material that allows for expansion and contraction and can be any structure capable of selective and variable expansion, contraction and density in response to applied forces. For example, when a force is exerted on a portion of the expandable member 110 in one direction (such as a force on a distal endpiece 112-2 connected to the expandable member 110), the expandable member 110 can be configured to expand. As depicted in FIGS. 1 and 2, the expandable member 110 can be configured to exhibit a substantially uniform shape when it expands.

Figure 3:
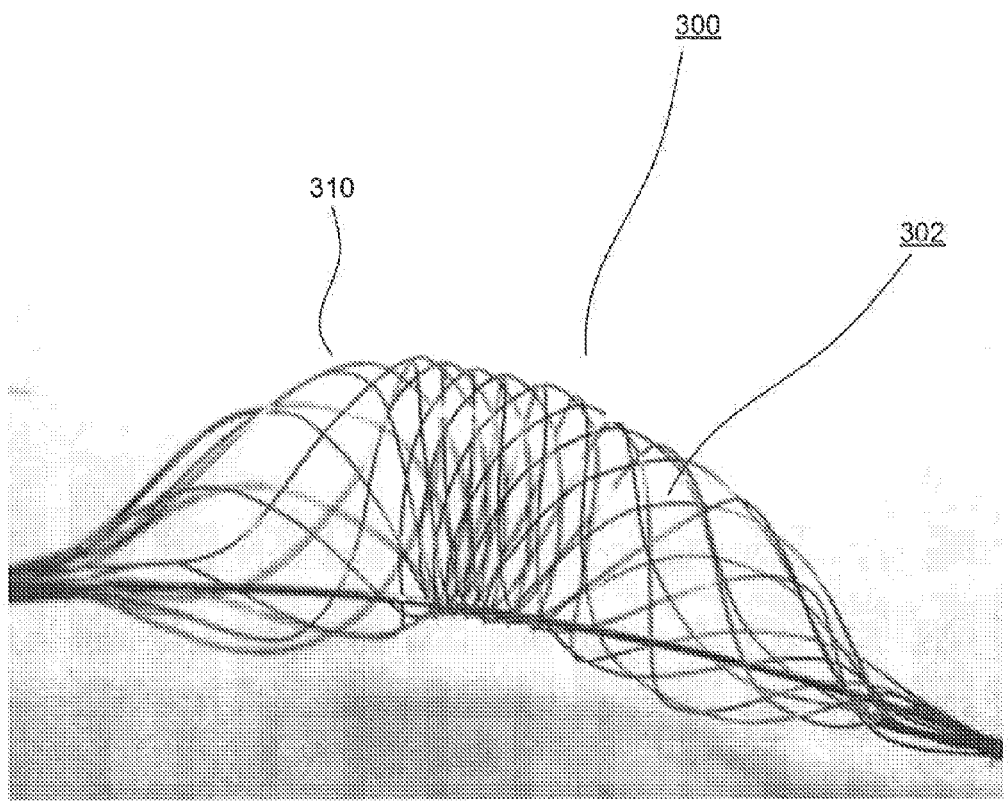
FIG. 3 is a perspective view depicting an asymmetrical shape of an expandable member consistent with the disclosure.

Alternatively, as depicted in FIG. 3, an expandable member 310 (as part of a device 300) can also be configured to exhibit a substantially asymmetrical shape when it expands. Consistent with the disclosure, an asymmetrical shape can improve an embodiment's ability to comply with the anatomy of a blood vessel.

When a force is exerted on the portion of the expandable member in another direction (e.g., a force on a distal connection point 112 of the expandable member 110 in a direction opposite the direction configured to cause expansion of expandable members), the expandable member can be configured to contract. According to another embodiment of the device, the expandable member can be configured to achieve higher filament density within portions of the expandable member in the device. In the embodiment shown in FIG. 1, for example, the expandable member 110 can include a filament mesh 102, where the filament material in the mesh can be wire.

In the embodiment shown in FIG. 1, the distal endpiece 112-2 of the expandable member 110 can be connected to a distal end 1 of an elongated control member 4 which can extend from a proximal end of a shaft 3. As used herein the term "connected" means linking, bringing, and/or joining together by any type of mechanical connection.

Figure 4:
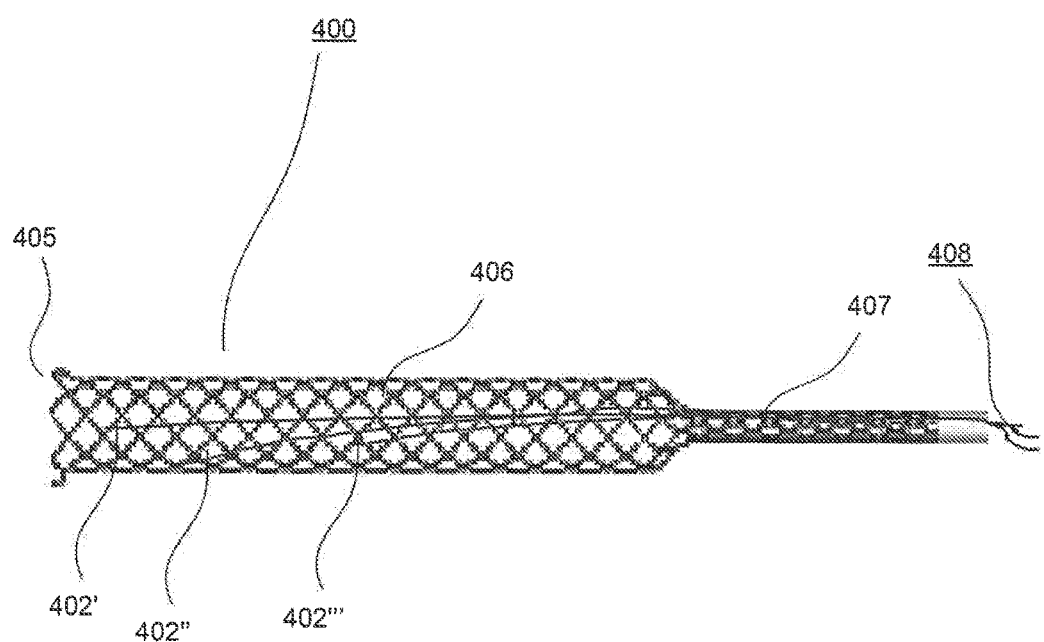
FIG. 4 is a perspective view of an embodiment of a device consistent with the disclosure exhibiting a substantially uniform girth and wire density.

According to another aspect, for example as illustrated in FIG. 4, device 400 can have an expandable member 406 where a distal end 405 of the expandable member 406 can be an open end. That is, the distal end 405 of the expandable member 406 can include an opening (exhibiting a substantially unobstructed channel within the expandable member 406 at the distal end 406), where the opening has a circumference value that is substantially equal to a girth of the expandable member 406 in an expanded configuration. The device 400 in FIG. 4 can be comprised of a collapsible, fully retrievable, controllable fine wire construction (i.e., expandable member 405) that is mounted on, is an extension of, or that is otherwise coupled to a shaft 407. The girth and the filament density of the device 400 can be controllably varied. One or more elongated control members 408 (e.g. two control filaments, three control filaments, four control filaments, etc.) can extend from the device 400 to a proximal end of the shaft 407. In the example illustrated in FIG. 4, the elongated control members 408 include three control filaments, each connected to, interwoven with, looped and/or knotted around a portion of the expandable member 406 in a different connection point location 402', 402" and 402'''. The distal end 405 of the device 400 can be designed to be atraumatic to the blood vessel. According to some embodiments, the device can also include ex-vivo elements such as insertion tool, torquer and luer. According to some embodiments the one or more control filaments can be wire and/or can be made from polymers, such as polyurethane, silicone etc. As used herein, a "substantially unobstructed" channel can include a open channel that accommodates control filaments that are interwoven with, looped, knotted, and/or otherwise connected to connection point locations on the expandable member as described herein—including an distal open channel of an expandable member that accommodates control filament(s) that are interwoven with, looped, knotted, and/or otherwise connected to the expandable member at the periphery of the distal open channel.

Figure 6:
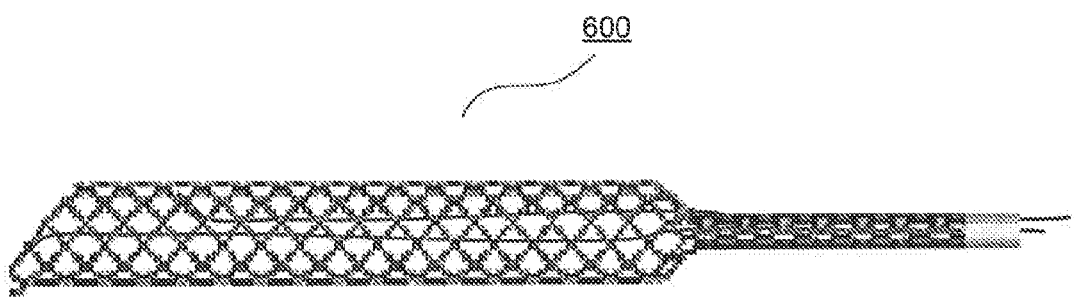
FIG. 6 is a perspective view of an embodiment consistent with the disclosure exhibiting an asymmetric distal end to facilitate improved clot penetration.
Figure 7:
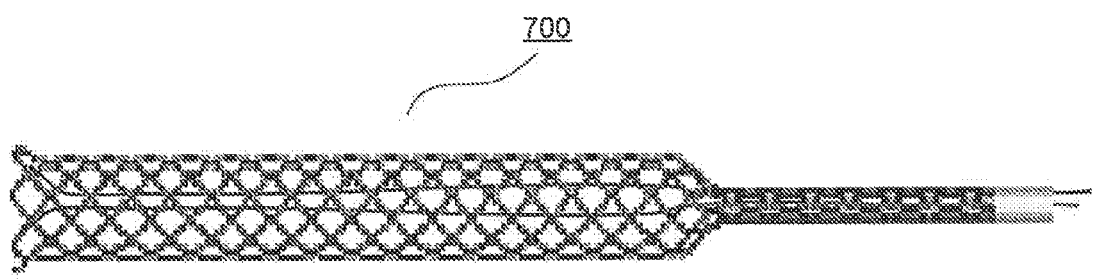
FIG. 7 is a perspective view of an embodiment consistent with the disclosure exhibiting elongated control members woven or otherwise incorporated into the expandable member.

In some embodiments the distal end (for example, and without limitation, the distal end 1 in FIG. 1 and the distal end 405 in FIG. 4) can be designed to be atraumatic to a blood vessel. For example, as illustrated in FIG. 1, the distal end 1 can be connected to an elongated, radio-opaque soft wire (such as guide wire tip). In another embodiment, illustrated in FIG. 4, the distal end 405 can be constructed of filaments (such as wires) that are looped back in an atraumatic fashion. For example, and without limitation, the filaments can be configured to include closed filaments loops at the distal end 405. Moreover, in an expanded configuration the loops of filaments at the distal end of the expandable member can be arranged in non-round and asymmetrical forms (e.g. as illustrated in device 600 of FIG. 6). These configurations can ease the advancement of a device in the vessel and/or can facilitate penetration to a thrombus or a blocked vessel. In another embodiment, a distal endpiece can reside inside the expandable member of the device, thereby eliminating the need for the elongated control member 4 to extend completely through the expandable member. In such an embodiment, a distal end of the device can resemble the branch connection point of an apple. The one or more elongated control members can be any elongated structures capable of exerting a force on an endpiece 112-2 (and/or, as appropriate, connection point locations 402', 402'', and 402''') of the expandable member. According to some embodiments, the elongated control members can be connected to a portion of the expandable member of the device, and can maintain the connection to the portion while undergoing pushing and pulling forces. Alternatively, the one or more elongated control members can be interwoven with, knotted and/or looped around a portion of the expandable member of the device (e.g. as illustrated, without limitation, in device 700 of FIG. 7). In addition, the one or more elongated control members can be filaments (such as wires) that are part of the expandable member at the distal end but that untie or are otherwise unwoven from the expandable member at the connection point locations and extend to the proximal part of the shaft. According to some embodiments, the elongated control members can terminate (or otherwise be connected to connection points) throughout the device (e.g. at proximal and/or middle portions of the expandable member) and/or at distal portions (including a distal connection point) of the expandable member. Alternatively, the elongated control members can extend beyond the distal endpiece 112-2.

The one or more elongated control members can be wholly or partially flexible, hollow and/or solid. Accordingly, the elongated control members can include, hut are not limited to, any filament, such as a shaft, a wire, or a rod. In an embodiment consistent with the disclosure, and as depicted for example in FIGS. 1 and 4, the elongated control members can be in the form of a wire.

Each elongated control member can be configured to apply force in concert with other control member or members and/or to apply force independently. In addition to the elongated control members, the treatment device can also include ex-vivo elements such as an insertion tool, a torquer, a luer, and one or more control handles.

As depicted in the figures, the elongated control members can be configured to reside within the shaft. For example, in FIG. 1 a proximal endpiece 1124 connected to the expandable member 110 can be connected to or otherwise coupled to a distal end of the shaft 3. In addition, the one or more elongated control members 4 can be connected to different connection point locations (such as connection point locations 402', 402'', and 402''' in FIG. 4) along the expandable member, and can extend through the center of the expandable member 110 and proximally inside the shaft 3. A further device—device 200 consistent with the present disclosure—is depicted in FIG. 2. The device 200 can include an expandable member 110 that can be mounted on or otherwise coupled to a shaft 3 as described above in connection with FIG. 1. As is also consistent with the current disclosure, the one or more elongated control members 4 in device 200 can be configured to be parallel to the shaft 3 rather than within shaft 3. That is, in device 200, the one or more elongated control members 4 can extend outside of the shaft 3 in a direction that is parallel to the longitudinal axis of the shaft 3.

While the preceding discussion referred primarily to the embodiments depicted in FIG. 1 and FIG. 2, it is understood that it also can apply to other embodiments, such as (without limitation) devices 300, 400, 500, 600, and 700 of FIGS. 3-7, as well as any other device described herein.

The one or more elongated control members can be configured to control the expansion of the treatment device at the target vessel. According to some embodiments the elongated control members can be controlled separately; alternatively the elongated control members can be controlled in concert. When one or more of the elongated control members undergo a pulling force in a proximal direction relative to the shaft, a diameter of the expandable member can be enlarged to exhibit a substantially uniform shape (or an asymmetrical shape) between the proximal end and the distal end of the expandable member. This can facilitate vessel compliance and adherence to the vessel wall. When the elongated control members undergo a pushing force, an outer diameter of the expandable member can be diminished, and the expandable member can be readily delivered to a treatment site or retrieved from treatment site. This control of the diameter of the expandable member at treatment sites can allow an operator of the device 100 (or any other devices illustrated in the figures) to perform gentle reposition maneuvers and/or can allow an operator to dislodge a coil ending if engaged in one of the cells.

Figure 5:
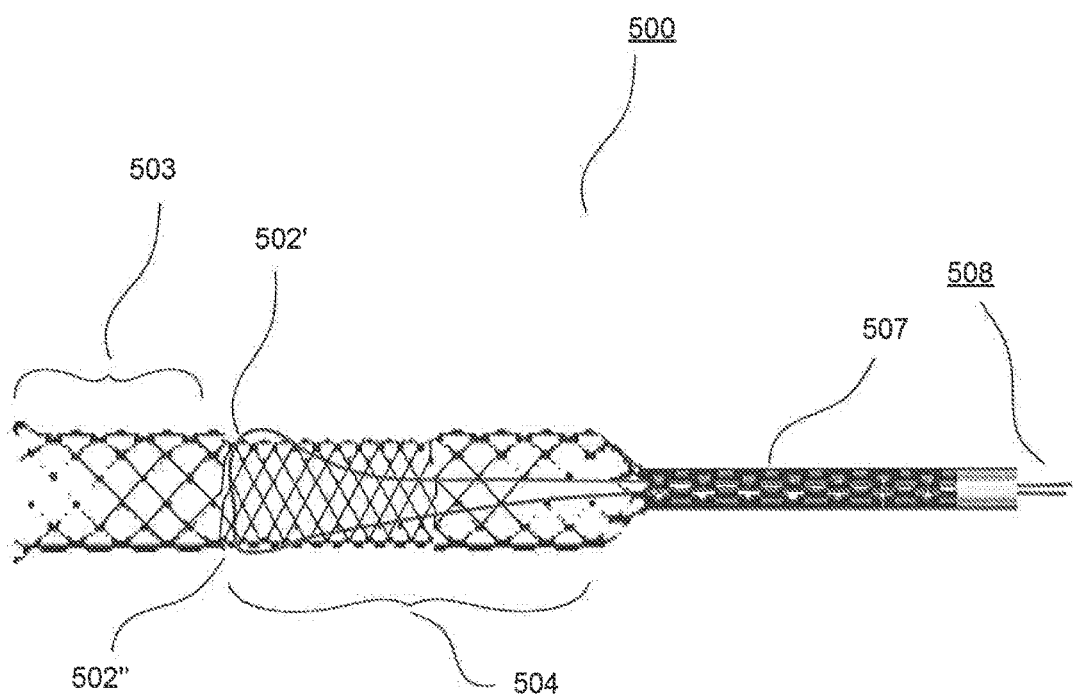
FIG. 5 is a perspective view of an embodiment of a device consistent with the disclosure exhibiting a variable girth and wire density.

FIG. 5 illustrates another embodiment of a device 500, where the elongated control members 508 can be configured to control the girth of a controllable portion 504 of the expandable member at the target vessel and/or to control the filament density (such as a wire density) of a controllable portion 504 of the expandable member. Consistent with this embodiment, control filaments associated with an elongated control member 508 can be interwoven, looped, and/or knotted with the filaments associated with the expandable member. According to an aspect of an embodiment, illustrated as device 500 in FIG. 5, if a control filament of an elongated control member 508 undergoes a pulling force in a proximal direction relative to the shaft 507, a girth of a controllable portion 503 (or a controllable portion 504) of the expandable member can be enlarged (or diminished) so as to exhibit a variable girth. This type of control can be used to facilitate vessel compliance and adherence to a vessel wall. As illustrated in FIG. 5, controllable portion 503 of the expandable member (i.e., the controllable portion of the expandable member from an open end exhibiting a substantially unobstructed channel to the region where a control filament associated with elongated control member 508 is looped into the expandable member, such as at connection point location 502' or connection point location 502") can be characterized by a girth and a filament density. Moreover, a controllable portion 504 of the expandable member (i.e., the controllable portion of the expandable member from the region where elongated control member 502 is looped into the expandable member to the distal end of shaft 507) can be characterized with a different girth and different filament density due to a pulling force on the respective control filament associated with elongated control member 508. When a control filament associated with the elongated control member 508 undergoes a pushing force (i.e., a force in the direction of the open end of the expandable member), a girth of a controllable portion 503 of the expandable member (i.e., the controllable portion of the expandable member from the region where the control filament associated with elongated control member 508 is looped into the expandable member such as connection point location 502' or connection point location 502" to the open end of the expandable member) can be variably diminished. In some embodiments it is not necessary to apply a pushing force to the elongated control members, only to release the pulling force. For example, the expandable member can be pre-biased to contract (or to expand), or otherwise configured to self-contract (or self-expand), in the absence of a pulling force. In other embodiments consistent with this disclosure, additional control filament(s) can be connected to, interwoven with, looped, knotted around, and/or otherwise connected other regions of the expandable member for additional control. For example, an additional elongated control member can be connected (or interwoven as discussed above, or as depicted in FIGS. 6 and 7) to distal, open end of device 500 so as to provide control to the expandable member as a whole—and/or to provide separate control of the controllable portion 503 of the expandable member. Further still, and without limitation, a further elongated control member can be connected to a region of controllable portion 504 that is between connection point location 502' (and/or connection point location 502") and shaft 507, so as to enable an additional controllable portion within controllable portion 50, where the additional controllable portion is proximal to shaft 507.

As aforementioned, the elongated control members can be also configured to control other properties of at least one controllable portion of the expandable member. For example, the elongated control members can be configured to control the filament density (such as the wire density) of the treatment device at the target vessel. If one or more of the elongated control members undergo a pulling force in a proximal direction relative to the shaft, the filament density of the expandable member can be made higher (e.g., controllable portion 504, in FIG. 5). Because more than one control filament can be used, the expandable member can achieve variable filament densities. The use of variable filament densities can assist in blocking blood flow to an adjacent aneurysm, and can assist in vessel compliance and adherence to the vessel wall. For example, when an elongated control member 508 undergoes a pushing force, a filament density of the controllable portion 504 of the expandable member can be diminished, and the expandable member can be readily delivered to a treatment site or retrieved from treatment site. Controlling the diameter of the expandable member at treatment sites can allow an operator of the device to perform gentle reposition maneuvers and/or can allow an operator to dislodge a coil ending if engaged in one of the cells.

The elongated control members can be also configured to turn the device (e.g., device 400 illustrated in FIG. 4) at the target vessel. If a control filament associated with an elongated control member undergoes a pulling force in a proximal direction relative to the shaft, while another control filament associated with the elongated control members is not pulled, or is pulled using a weaker force, then the expandable member can bend. This can be used to steer the device if it is advanced distally. Moreover, if one of the control filaments associated with an elongated control member undergoes a pushing force in a distal direction relative to the shaft, while another of the control filaments associated with the elongated control members is not pushed, or is pushed using a weaker force, then the expandable member can also bend.

Figure 8A:
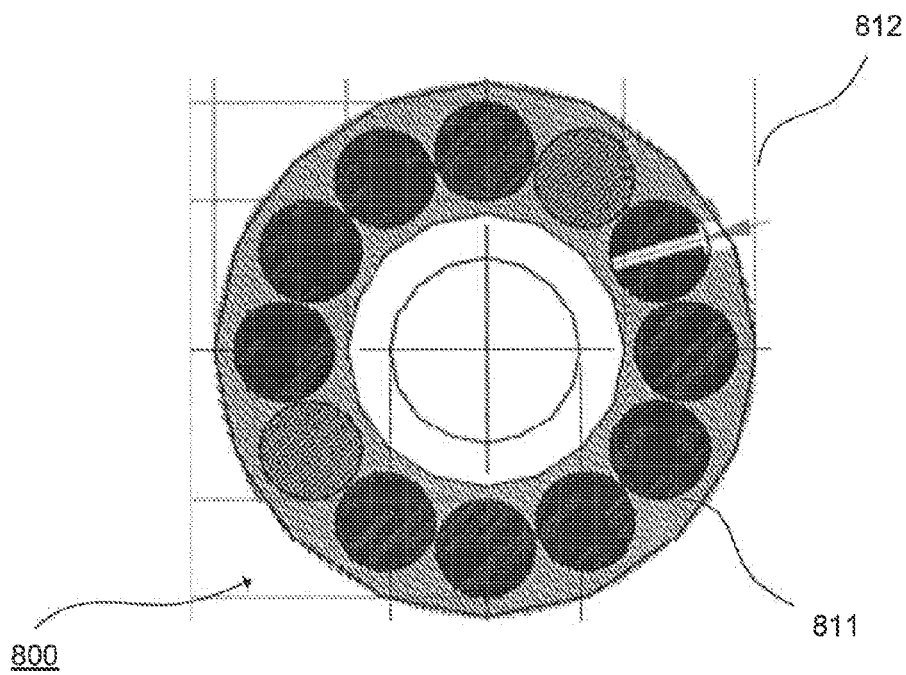
FIG. 8A is a perspective view of a connector consistent with the present disclosure.

In FIG. 8A an end 812 consistent with the disclosure is depicted. Apertures 811, which can accommodate the filaments that make up the mesh of the expandable member (not shown) are shown in a cylindrical arrangement.

When the device according to any of the embodiments is used in the human neurovasculature, it can be flexible and have a small form factor. In general, neurovascular devices can be configured to be delivered through supple microcatheters which have a small internal diameter of about 0.5 mm. As a result, an exemplary device of the present disclosure can be configured to have a minimal outer diameter when collapsed during delivery.

Figure 8B:
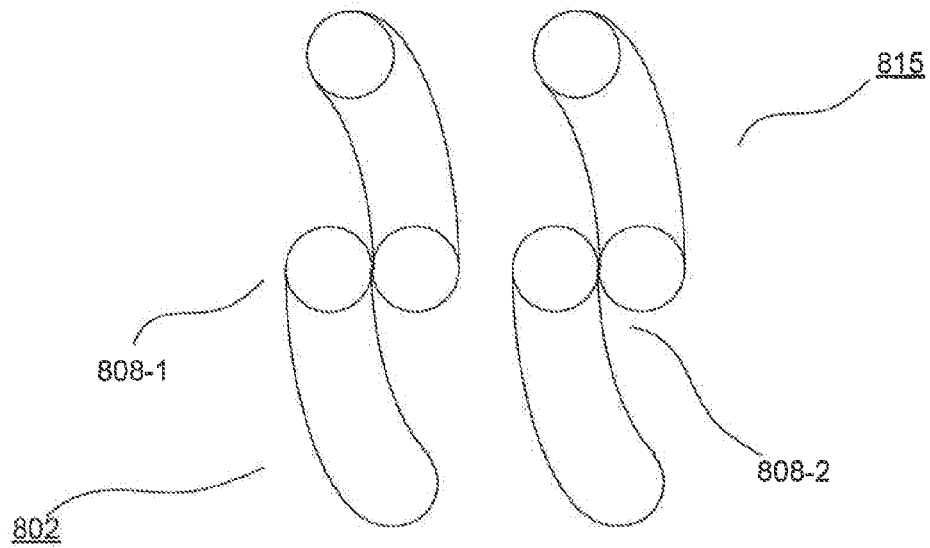
FIG. 8B is a perspective view depicting a minimum diameter of a collapsed expandable member as a function of wire diameter.

For example, the expandable member according to any of the embodiments can be configured to have a minimum profile. Consistent with the disclosure, there can be filament crossings at an intermediate region of the filament mesh of the expandable member. That is, in an embodiment consistent with the disclosure, the diameters of four filaments can be considered in determining a minimum outer diameter of the expandable member when the device is sheathed. More specifically, in an embodiment depicted in FIG. 8B, a first crossing point 808-1 of two filaments of a filament (such as filament mesh 102 in FIG. 1) on one portion of the expandable member cannot be smaller than the diameter of two filaments that cross at the first crossing point 808-1. In a minimum configuration, and due to the symmetry of the expandable member, there can be a second crossing point 808-2 diametrically opposite the first crossing point 808-1, and subject to the same minimal thickness. Accordingly, a minimum thickness of the filament mesh of the expandable member when collapsed can be expected to be determined by the thickness of four filament diameters (a configuration 815 depicted in FIG. 8B). This can occur in an intermediate region of the expandable member (i.e., the region between a proximal region of the expandable member near a proximal endpiece and a distal region of the expandable member near a distal endpiece).

Figure 8C:
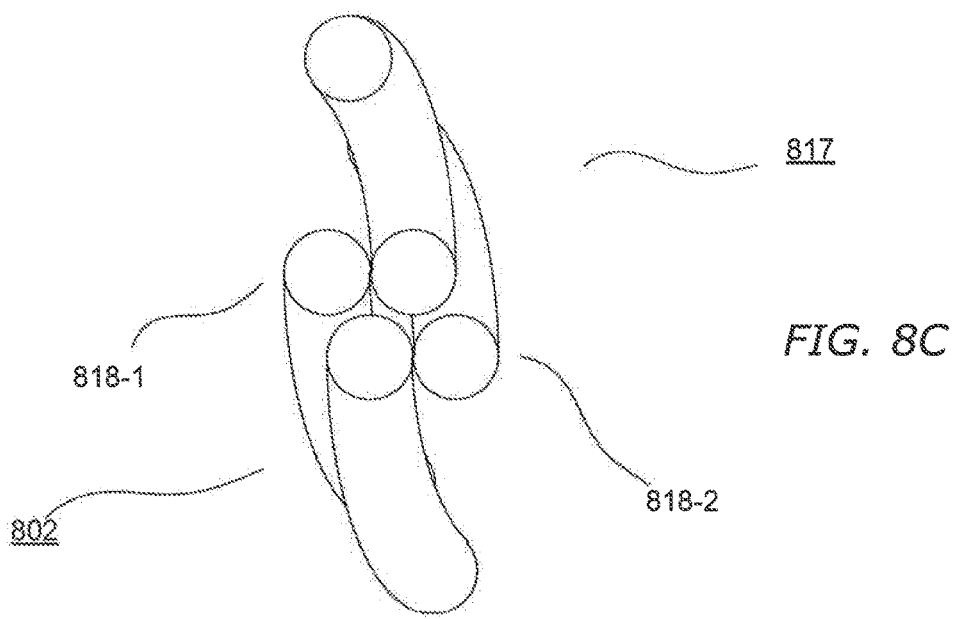
FIG. 8C is a perspective view depicting a minimum diameter of a collapsed expandable member as a function of wire diameter where the wires are ordered near a connection point.

Nonetheless near a proximal endpiece, (and in some embodiments a distal endpiece), the filaments that make up the filament mesh can be ordered one on the side of the other such that a minimal outer diameter of the expandable member is determined by only two filaments (rather than four). This ordered arrangement, when the filament mesh is collapsed, is depicted in FIG. 8C—which depicts a similar first crossing point 818-1 and a similar second crossing point 818-2. As a result of the configuration 817 depicted in FIG. 8C, the total diameter of the filament mesh, when collapsed, can be minimal.

Figure 8D:
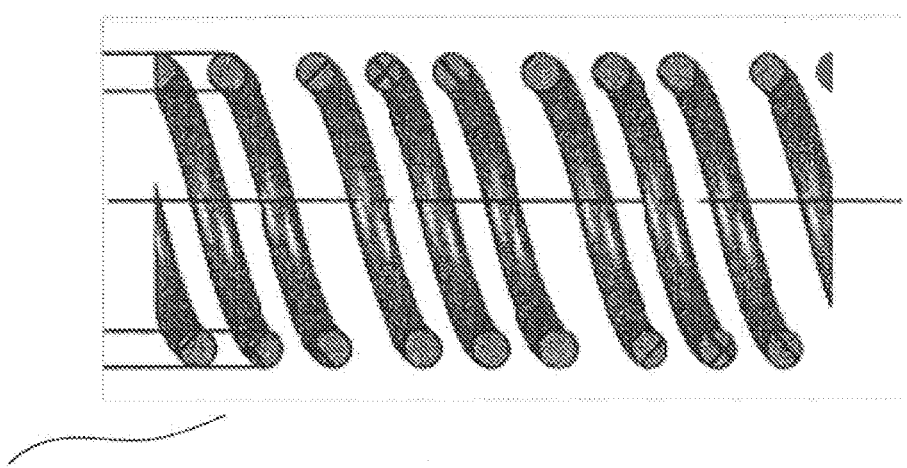
FIG. 8D is a perspective view of a coiled wire arrangement at a connection point.

Alternatively, the filaments that make up the filament mesh can be coiled at the proximal and/or distal ends of the expandable member, as in configuration 819 depicted in FIG. 8D, to achieve a similar effect. When the filaments are coiled opposite a filament mesh region, an endpiece may not be necessary to transition a plurality of filaments from a shaft region of a device to a proximal region of the expandable member.

Figure 9:
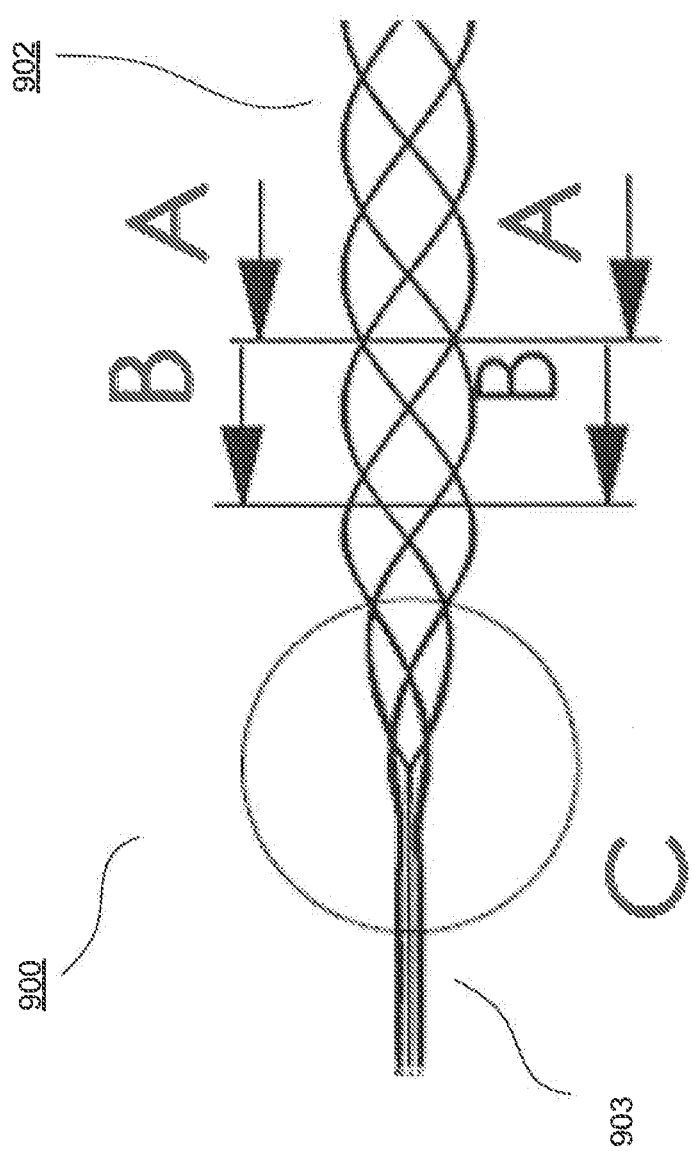
FIG. 9 depicts an embodiment consistent with the disclosure utilizing eight filaments, where the filaments are parallel to a shaft axis in the region of the shaft.

In an embodiment consistent with the disclosure a filament arrangement 900, as depicted in FIG. 9, can be utilized. The embodiment disclosed in FIG. 9 depicts eight filaments transitioning from a shaft region 903 to a filament mesh 902. In the shaft region 903, the eight filaments are depicted as oriented parallel to a shaft axis.

Figure 10B:
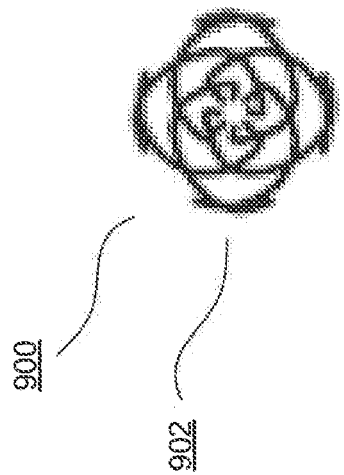
FIGS. 10A-B depict perspective views of the embodiment of FIG. 9 along selected planes.
Figure 10A:
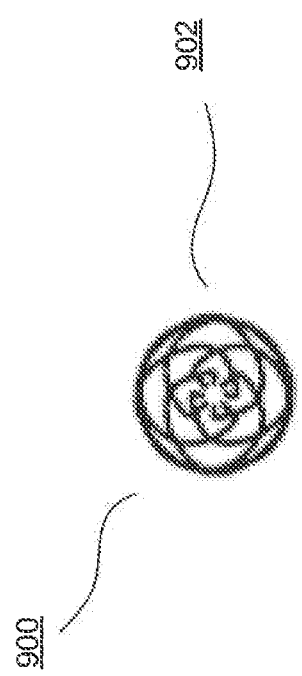

FIG. 10A depicts a view along a cross section of the filament arrangement 900, and depicts eight filaments forming a filament mesh 902 from a minimal diameter. FIG. 10B depicts a view parallel to the view of FIG. 10A, but closer to the transition region from the shaft region 903. FIG. 10C depicts further detail of eight filaments transitioning from a shaft region 903 to a filament mesh 902. In the depicted embodiments of FIGS. 9 and 10A-C, there is no endpiece shown (such as the endpiece 812 of FIG. 8A). Among other things, where the filaments that make up the filament mesh transition from an orientation that is parallel to a shaft axis in a shaft region to a filament mesh, the use of an endpiece can maintain the arrangement of filaments to ensure that a minimal cross section is presented near the endpiece while still maintaining a hollow center region through which an elongated control member may reside.

Figure 11:
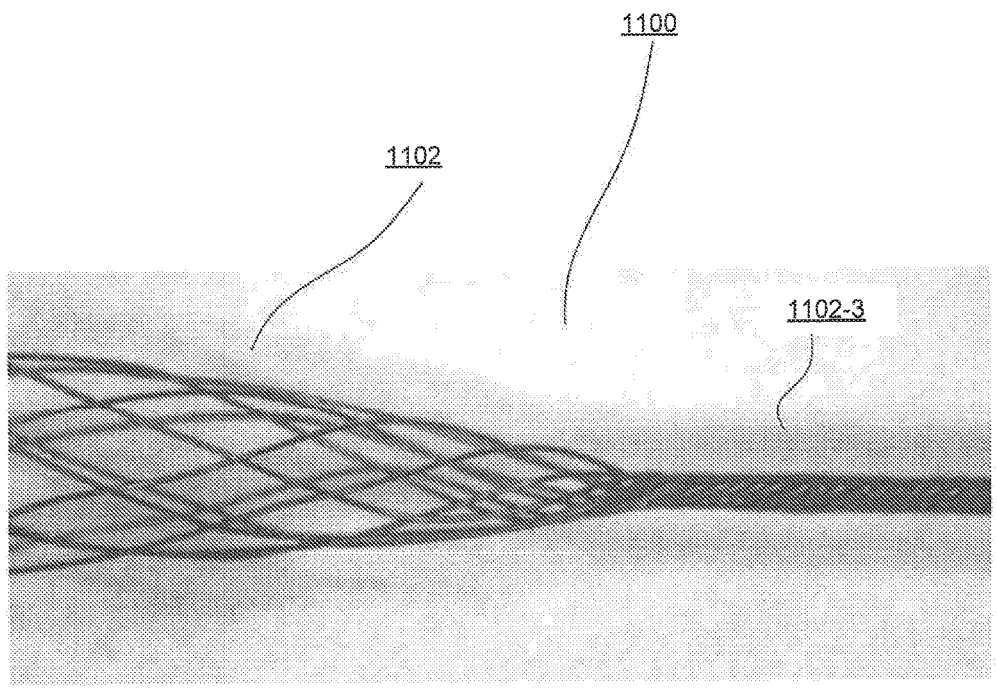
FIG. 11 depicts an embodiment consistent with the disclosure utilizing twelve filaments, where the filaments are coiled around a shaft axis in the region of the shaft.

In another embodiment consistent with the disclosure, a filament arrangement 1100, as depicted in FIG. 11, can be utilized. The embodiment disclosed in FIG. 11 depicts twelve filaments transitioning from a shaft region 1102-3 to a filament mesh 1102. In the shaft region 1102-3, the 12 filaments are coiled about a shaft axis. For the embodiment shown in FIG. 11, the use of an endpiece can be optional.

Figure 12:
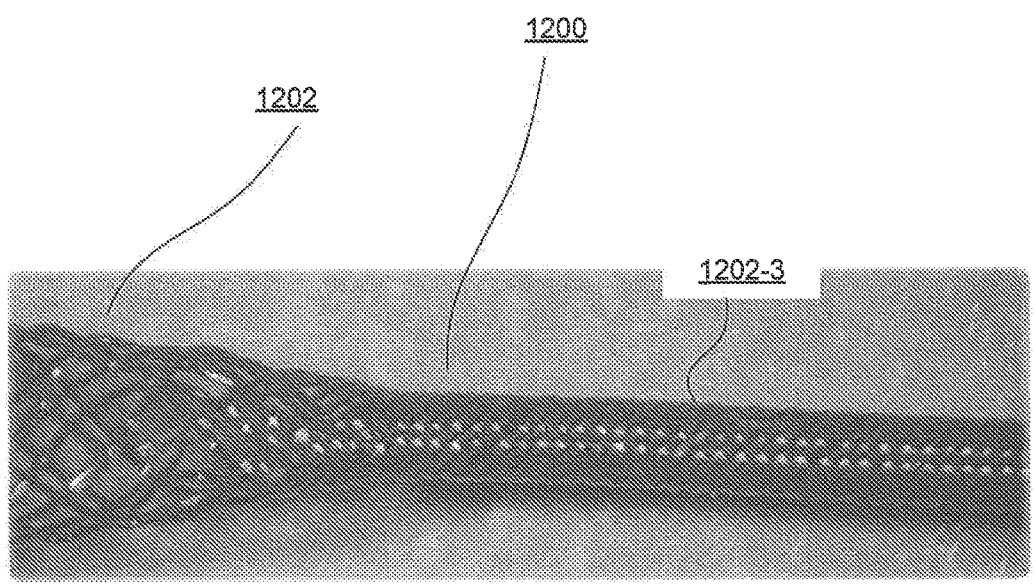
FIG. 12 depicts a further embodiment consistent with the disclosure utilizing twelve filaments, where the filaments are coiled around a shaft axis in the region of the shaft.

In another embodiment consistent with the disclosure, a filament arrangement 1200, as depicted in FIG. 12, can be utilized. The embodiment disclosed in FIG. 12 depicts twelve filaments transitioning from a coiled shaft region 1202-3 to a braided filament mesh 1202. In the coiled shaft region 1202-3, the twelve filaments can be coiled about a shaft axis. Again, for the embodiment shown in FIG. 12, the use of an endpiece can be optional.

Figure 13:
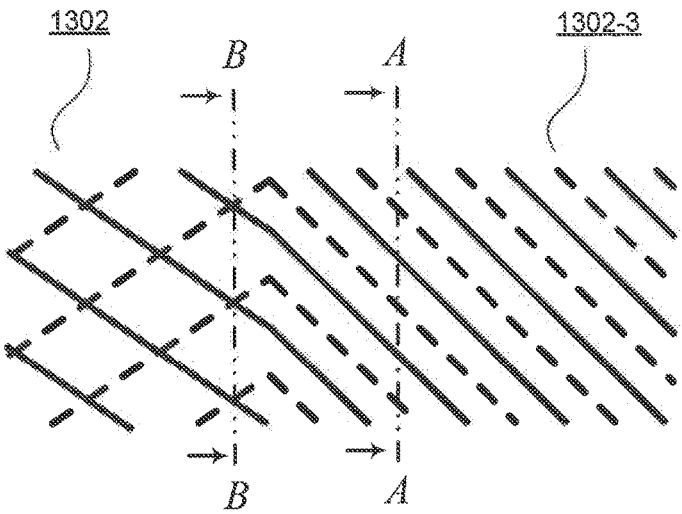
FIG. 13 is a diagram indicating an arrangement of filaments consistent with the disclosure in a region transitioning from a shaft region to a proximal end of an expandable member without an endpiece.
Figure 14:
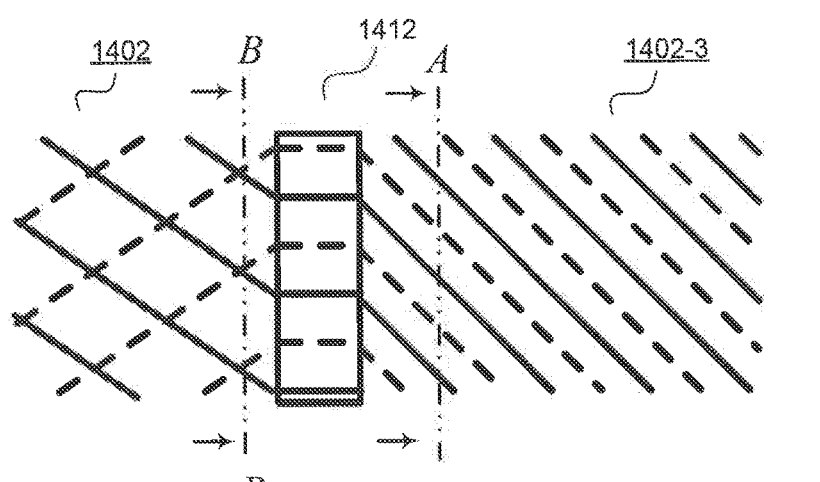
FIG. 14 is a diagram indicating an arrangement of filaments consistent with the disclosure in a region transitioning from a shaft region to a proximal end of the expandable member with an endpiece.
Figure 15:
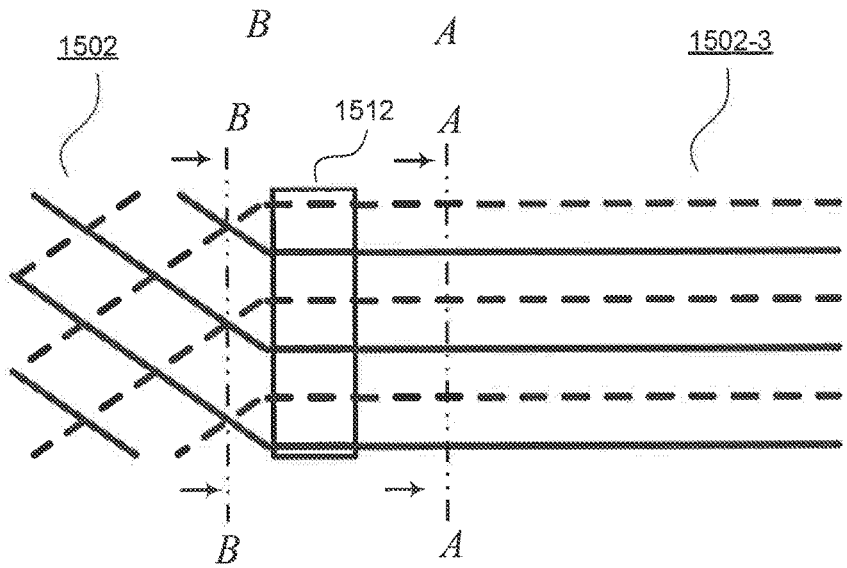
FIG. 15 is a diagram indicating another arrangement of filaments consistent with the disclosure in a region transitioning from a shaft region to a proximal end of the expandable member with an endpiece.

FIGS. 13-15 provide diagrams indicating arrangement of filaments consistent with the disclosure in a region transitioning from a shaft region to a proximal end of the expandable member. For purposes of clarity only, the alternating filaments that make up the filament mesh in FIGS. 13-15 are shown as either solid lines or dashed lines. The arrangement depicted in FIG. 13 is similar to that depicted in FIGS. 11 and 12, and shows a transition from a series of coiled filaments (in shaft region 1302-3) to a filament mesh 1302. In FIG. 13, there is no endpiece depicted.

The arrangement depicted in FIG. 14 is similar to that depicted in FIG. 13, and shows a transition from a series of coiled filaments (in shaft region 1402-3) to a filament mesh 1402. In FIG. 14, there is depicted an endpiece 1412, which can be used to maintain the coil in shaft region 1402-3 while the mesh in the filament mesh 1402 expands or contracts under control of an elongated control member (not shown).

The arrangement depicted in FIG. 15 is similar to that depicted in FIGS. 9 and 10A-C, and shows a transition from a series of parallel filaments (in shaft region 1502-3) to a filament mesh 1502. In FIG. 15, there is also depicted an endpiece 1512, which can be used to maintain the arrangement of the filaments in the shaft region 1502-3 while the mesh in the filament mesh 1502 expands or contracts under control of an elongated control member (not shown).

FIGS. 13-15 also include lines indicating a plane "A" (which is in a shaft region) and a plane "B" (which is in a filament mesh region). The plane "B" is selected to pass through the filament mesh region at a point where filaments cross.

Consistent with the disclosure, FIGS. 16A-D depict exemplary "slices" along plane "A" and plane "B" for a six-filament arrangement (FIGS. 16A and 16C) and for a twelve-filament arrangement (FIGS. 16B and 16D).

FIGS. 16A and 16B depict an arrangement of filaments 1602 that are in a single-file continuum about an axis. That is, as used herein, a single-file continuum of filaments about an axis means filaments arranged such that the filament cross-sections lie one after another in a loop about the axis, without the filament cross-sections lying in a substantially stacked configuration relative to the axis. Moreover, a "loop" means any simple closed curve or a combination of lines and curves that connects to itself, such as a circle, oval, square, rectangle, triangle, etc. In contrast, FIGS. 16B and 16D depict an arrangement of filaments 1602 that are not in a single-file continuum about an axis, but are in a substantially stacked configuration near and at filament crossing points.

Moreover, although the endpiece 812 shown in FIG. 8A depicts apertures in a one-to-one relationship with filaments, one of ordinary skill in the art would appreciate that an endpiece consistent with this disclosure can include one or more channels (each channel of which can accommodate several filaments in a single-file continuum configuration) rather than the configuration of apertures of endpiece 812.

Figure 17:
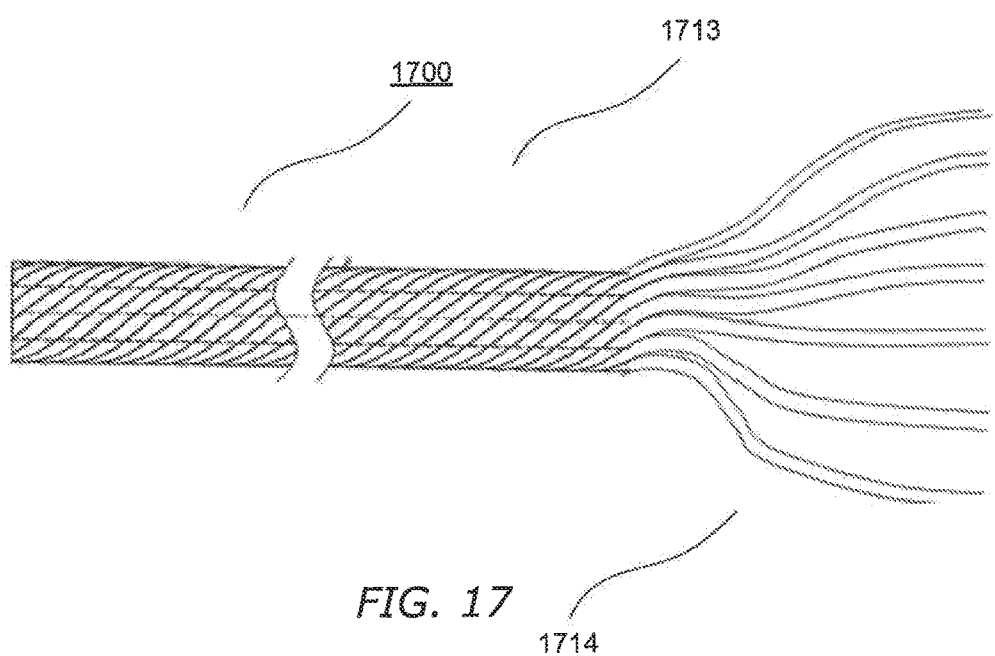
FIG. 17 is a perspective view of a device for treatment with a shaft including a hollow torque cable tube in a wound and unwound state.
Figure 18:
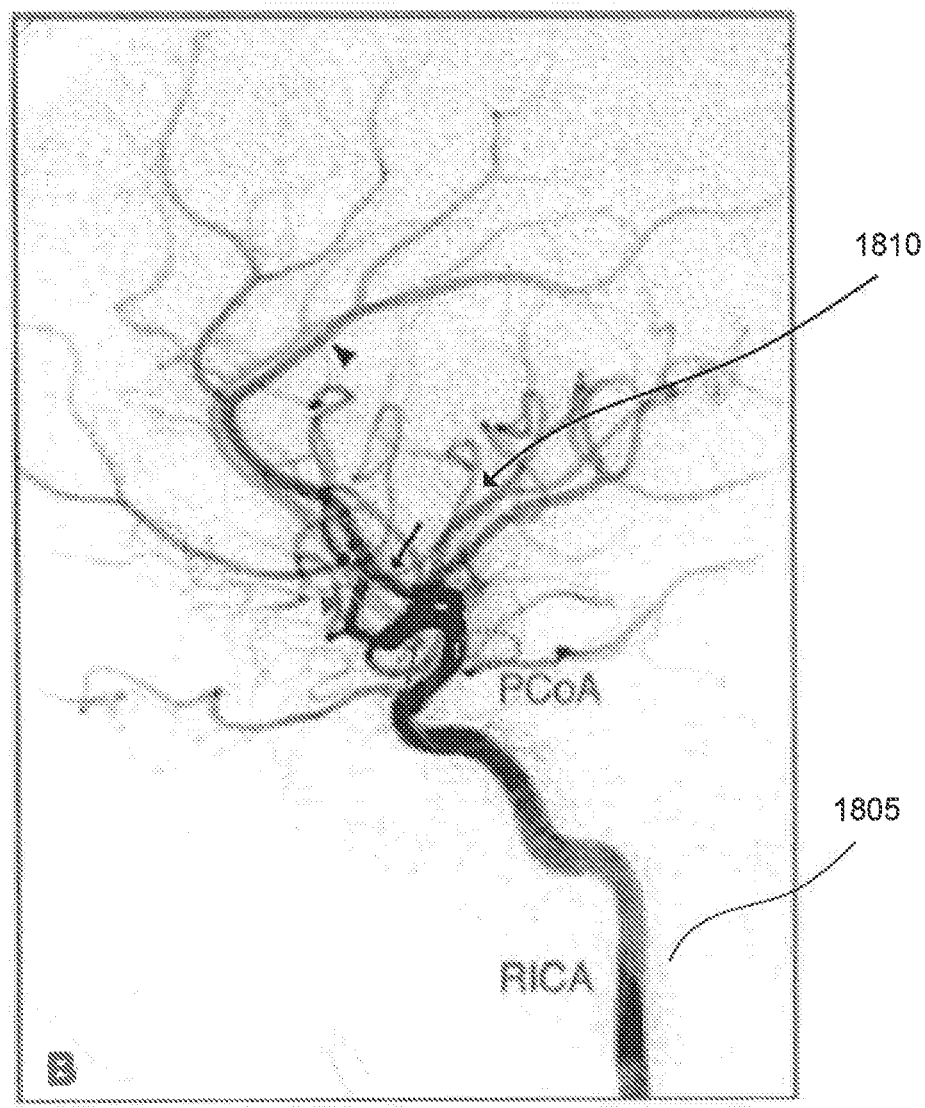
FIG. 18 depicts blood vessels leading to the brain, depicting variable tortuosity and vessel diameters.

Further still, as depicted in FIG. 17 (and similar to the embodiments of FIGS. 11-13), a device consistent with this disclosure can be configured to provide a minimal profile by including a hollow torque cable 1700, which can include a wound portion 1713 and an unwound portion 1714. By way of example only, the shaft 3 of FIGS. 1 and 2 (and corresponding shaft elements of FIGS. 3-7) can include the wound portion 1713 of the hollow torque cable 1700, and the expandable member can be configured from the filaments (such as wires) of the hollow torque cable 1700 in the unwound portion 1714. Such a configuration can exhibit an optimal profile because no additional connecting media (such as endpiece 812 depicted in FIG. 8A) is required. In any of the embodiments discussed here, however, (including without limitation all of the embodiments depicted in FIGS. 9-17) a shaft and an expandable member can also be welded or soldered together consistent with the disclosure, and can achieve minimal profile. The shaft can be welded or soldered to the expandable member with or without the use of an endpiece. Further still, a shaft and an expandable member can be connected using a heated polymer or glue to bond the filaments. In this way, even if a rigid region is required along a portion of the shaft of the device as a whole (as can preferably be required for control and/or an additional connection region between the torque cable and a portion of a shaft of the device as a whole) the rigid region can be distant from a more flexible, distal region of the device and can be located in a larger more proximal vessel. For example, in the case of an intracranial aneurysm, a rigid region (as may be useful as a control point and or establishing a connection between a torque cable and a further shaft) can be located in the common carotid artery. Such a circumstance is depicted in FIG. 18, which shows a carotid artery 1805, and which can accommodate a region of a shaft with more rigidity than can the target location 1810. Accordingly, a rigid connection region between the torque cable and a shaft can be located distant from target location 1810—which is where an expandable member (and a more flexible portion of the device as a whole) is targeted to be positioned and manipulated.

Returning to FIG. 17, FIG. 17 depicts the transition from the wound portion 1713 of the hollow torque cable 1700 to the unwound portion 1714. According to some embodiments the dimensions and construction of the filaments (or wires) can be also determined by the dimensions of the neurovascular microcatheter described above. The diameter of the some of the filaments described above can be between 50 μm and 120 μm (e.g. 75 μm). The dimensions of the elongated control members can be smaller than 50 μm (e.g. 25 μm or 10 μm).

Further still, a device with the specified filament arrangements (as depicted in FIGS. 9-17) on only the proximal or distal region of the expandable member is also consistent with this disclosure. By the way of example only, a device can have an expandable member with an open distal end. The filaments of the expandable member can be connected as described above to the shaft at the proximal end but can be looped back at the distal without being closed or connected again. In yet another example, the filaments at the distal end can be connected together without arranging them in the low profile arrangement described herein.

The expandable member can be made of any suitable flexible material known to those skilled in the art. Suitable expandable materials can include, but is not limited to, polymers, metals, metal alloys, and combinations therefore. In an embodiment, for example, the expandable member can be constructed from super elastic metals such as Nitinol with minimal outer diameter. In order to visualize the expandable member with angiographic imaging, the expandable member can further include a radio-opaque marker and/or material. For example, in an embodiment, the expandable member can include a plurality of Nitinol wires with a core made of Tantalum or Platinum metals. The radiopaque core can be 20% to 50% by volume (e.g. 30% or 40%). In an additional embodiment, the wires of the expandable member can be made to be radiopaque by deposition of a thin layer of radiopaque metal such as Platinum.

Figure 19:
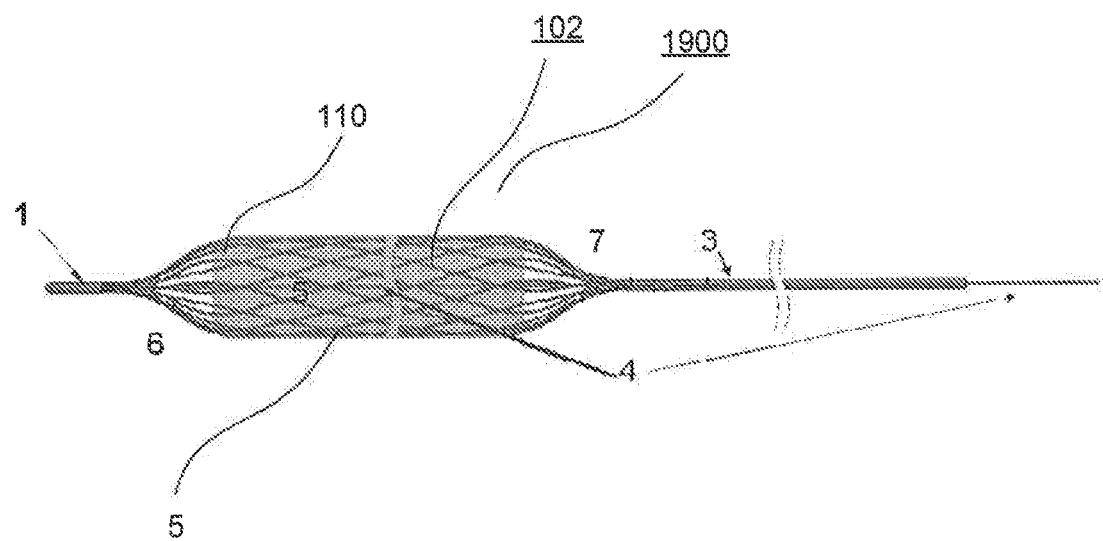
FIG. 19 is a perspective view of a further embodiment consistent with the disclosure.

The device according to any of the embodiments in the figures for treating a medical condition (e.g., an aneurysm or biliary tract) can further be configured to reduce the risk of coil herniation into the parent vessel. For example, in an embodiment, the size of the cells (i.e., the spaces within the filament mesh of the expandable member) which are aligned to the vessel wall can be minimal. On the other hand, as illustrated in FIG. 19 in a device 1900, to allow continuous blood flow during operation, a proximal cell 7 and a distal cell 6 can be relatively large. Therefore the filament mesh 102 can be configured to exhibit different cell sizes and shapes. For example, the density of the cylindrical area which is aligned to the vessel wall can be 3 to 12 crossings per centimeter while the density of transition and conical area (the proximal and distal portion) can be 1 to 5 crossings per centimeter. As described above, the elongated control members can control the mentioned cell size and density of the expanded member. Using the elongated control members, a variable cell size can be achieved. Consistent with a further embodiment, the filament mesh 102 can be configured to exhibit a relatively large concentration of filaments in the portion of the device that is facing the aneurysm neck. In yet another embodiment the aneurysm facing portion (cylindrical) can be constructed of wound filaments. In one embodiment the spacing between the windings of the wound wires can be controlled using the one or more control filaments associated the elongated controlled members. These control filaments can also be partially wound with the filaments of the expandable member (illustrated in FIG. 7).

Consistent with yet another embodiment, and depicted in FIG. 19 as the device 1900, a main body 5 of the cell structure of the expandable member 110 can be covered completely or partially to achieve full blockage of the aneurysm neck. The covering of the cell structure of the expandable member can be achieved by using a variety of medical grade polymers, such as polyurethane, silicone etc. The covering of the cell structure of the expandable member can also be achieved with organic tissue such as Pericardium. This option can provide assistance in the case of a ruptured aneurysm, because the physician can block the aneurysm until it is embolized. While not depicted, a main body of the cell structure of the expandable member 310 in FIG. 3 can also be covered completely or partially to achieve full blockage of the aneurysm neck. In a further embodiment consistent with the disclosure, a method to block a ruptured aneurysm can include providing a pulling force on the one or more elongated control members 4 until the filament mesh 102 exhibits cells sufficiently small so as to substantially prevent blood flow into the aneurysm. In addition, the filaments of the filament mesh 102, the covering over the main body 5, or both can be configured to be drug eluting during the use of the device 1900. Moreover, the filaments of the filament mesh 102 can be covered with materials which expand upon interaction with liquids (for instance, hydrogels). Furthermore, the filament mesh 102 can be made of two or more layers of braided filaments (such as two or more layers of braided wires).

Figure 20:
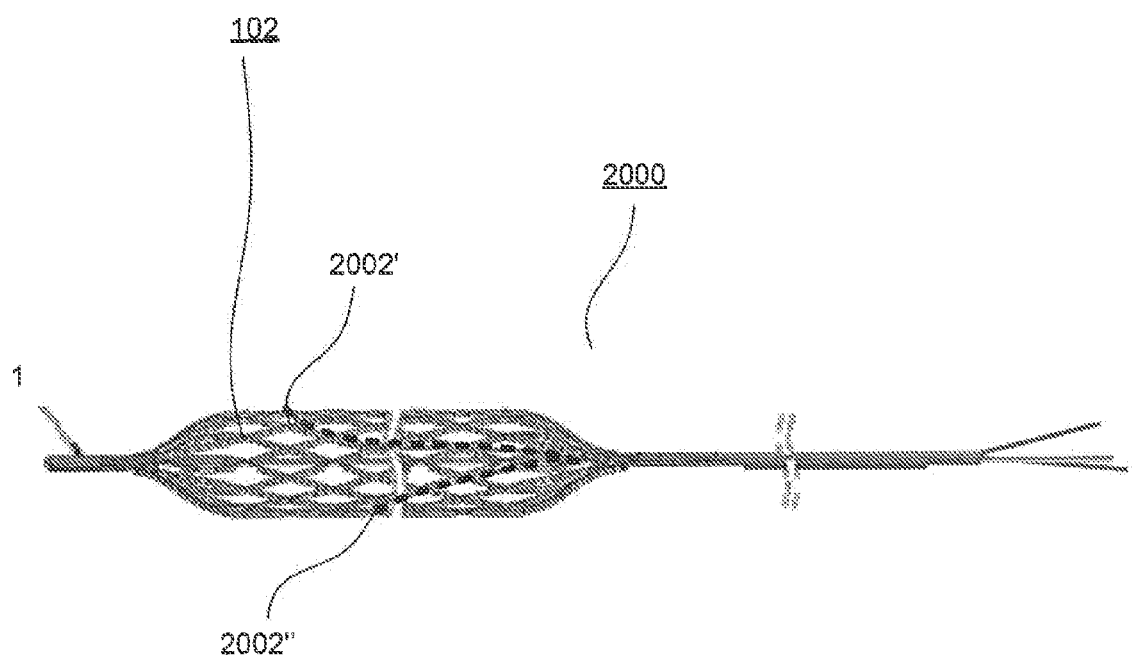
FIG. 20 is a perspective view of a further embodiment consistent with the disclosure.

FIG. 20 illustrates device 2000 that is similar in some ways to the device disclosed in reference to FIG. 19 and has several control filaments associated with an elongated control member. Each of the control filaments associated with the elongated control member can be connected, looped, and/or knotted to the filament mesh 102. In FIG. 20 there are two control filaments shown for clarity; however more control filaments associated with an elongated control member can be used consistent with this disclosure. The control filaments associated with elongated control members can be connected to filament mesh 102 at distinct connection point locations 2002' and 2002" along the body of expandable member. Consistent with the discussion above in connection with FIGS. 4 and 5, and without limitation, device 2000 can be configured to include controllable portions that exhibit variable girth and filament density under control of the elongated control members.

Figure 21:
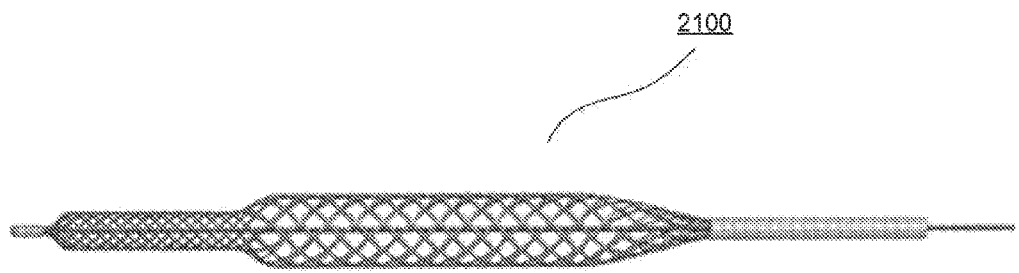
FIG. 21 is a perspective view of another embodiment consistent with the disclosure, including an expandable member exhibiting at least two substantially uniform shapes between its proximal end and its distal end.

In a further embodiment, a device consistent with this disclosure can be configured to address the clinical needs of the aneurysm coiling procedure. Because aneurysms usually occur at bifurcations and branches of arteries, the shape of the device can be configured to achieve improved vessel compliance at these anatomies. For example, the device 2100, depicted in FIG. 21, can be configured to exhibit at least two substantially uniform shapes between the proximal end and the distal end of the expandable member in the expanded configuration. In an embodiment consistent with the disclosure, there are at least two substantially uniform shapes. Further still, the device 300, depicted in FIG. 3 can be configured to exhibit at least two asymmetrical shapes between the proximal end and the distal end of the expandable member 310, or at least an asymmetrical shape with another uniform shape. For example, a combination of shapes can include a pear-shape, which can be used for treating endovascular aneurysms.

Figure 22:
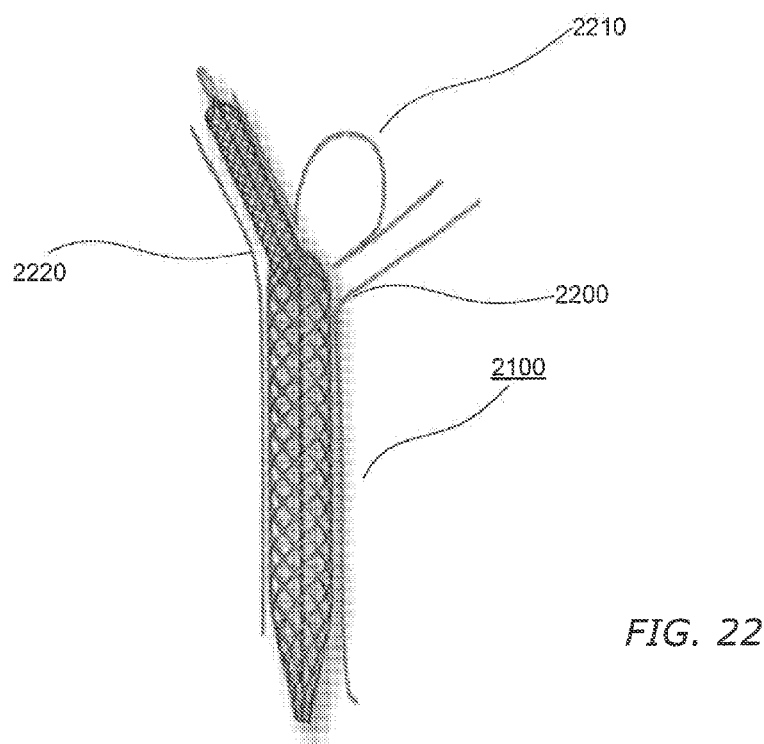
FIG. 22 is a perspective view of the device of FIG. 21 in a bifurcated vessel.
Figure 23:
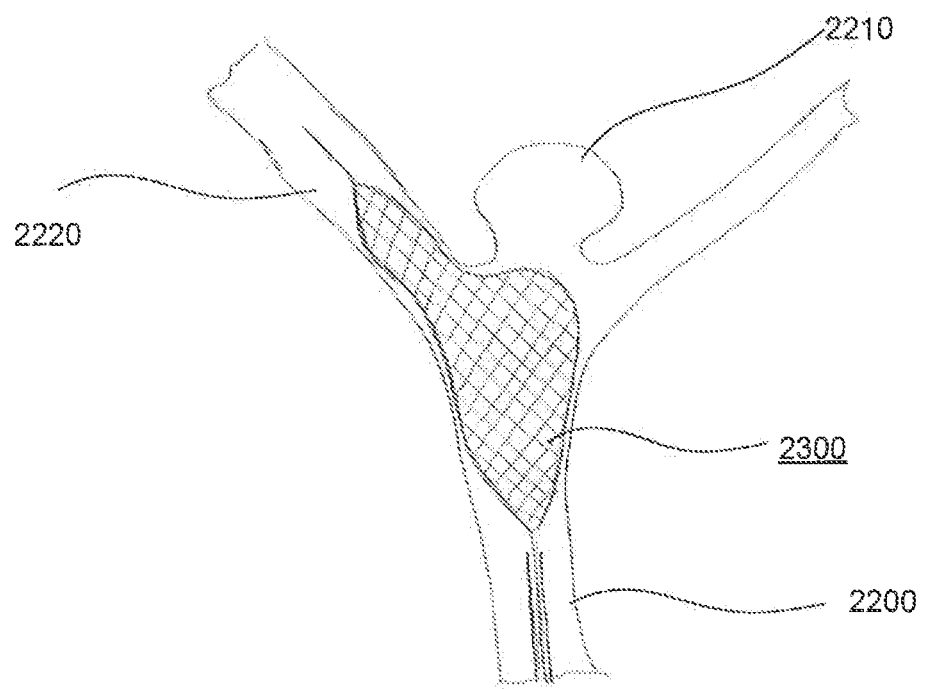
FIG. 23 depicts a further asymmetrical pear-shaped expandable member optimized to comply to bifurcated vascular regions.

In the embodiment depicted in FIG. 22, the pear-shaped configuration of the device 2100 can be used to treat an aneurysm 2210 located at the tip of a basilar artery. In use, the device 2100 can be deployed across the bifurcation extending from one bifurcated vessel 2220 to the parent vessel 2200. Moreover, in alternative embodiments, a device for treating endovascular aneurysms consistent with the current disclosure can include any suitable variable outer diameter in order to achieve the same effect as shown with the pear-shaped configuration. In addition, all or part of the features of the pear-shaped configuration can be utilized with all or part of the features previously described above in connection with any of the devices described herein. Moreover, in yet alternative embodiments, a device for treating endovascular aneurysms consistent with the current disclosure can be controlled via the one or more elongated control members to achieve a variable outer diameter in order to achieve the same effect as shown with the pear-shaped configuration. By way of example only, and without limitation, FIG. 23 depicts a pear-shaped expandable member 2300 deployed across the bifurcation depicted in FIG. 22.

In a further embodiment consistent with the disclosure, any of the devices described herein can include a detachment mechanism configured to enable the expandable member to detach from the shaft and remain as a permanent support scaffold at the vessel. The detachment mechanism can be useful in circumstances where a physician is concerned about a prolonged embolization time inside the aneurysm. In addition, the detachment mechanism can serve as a safety feature in case coil herniation occurred during the procedure and cannot be resolved with the control filament (such as the one or more elongated control members). The detachment mechanism can be electrical, mechanical or chemical and can be configured to allow a physician to first determine the final dimensions of the expandable member (using a control filament or the one or more elongated control members) and then detach the expandable member in its desired configuration. For example, in an embodiment consistent with the disclosure, an electric fuse can be located at a detachment connection point between the proximal end of the expandable member and the distal end of the shaft. The electric fuse can be configured to connect the one or more elongated control members to the expandable member, thereby attaching the expandable member to the shaft, and further can be configured to detach the expandable member from the shaft.

Figure 24:
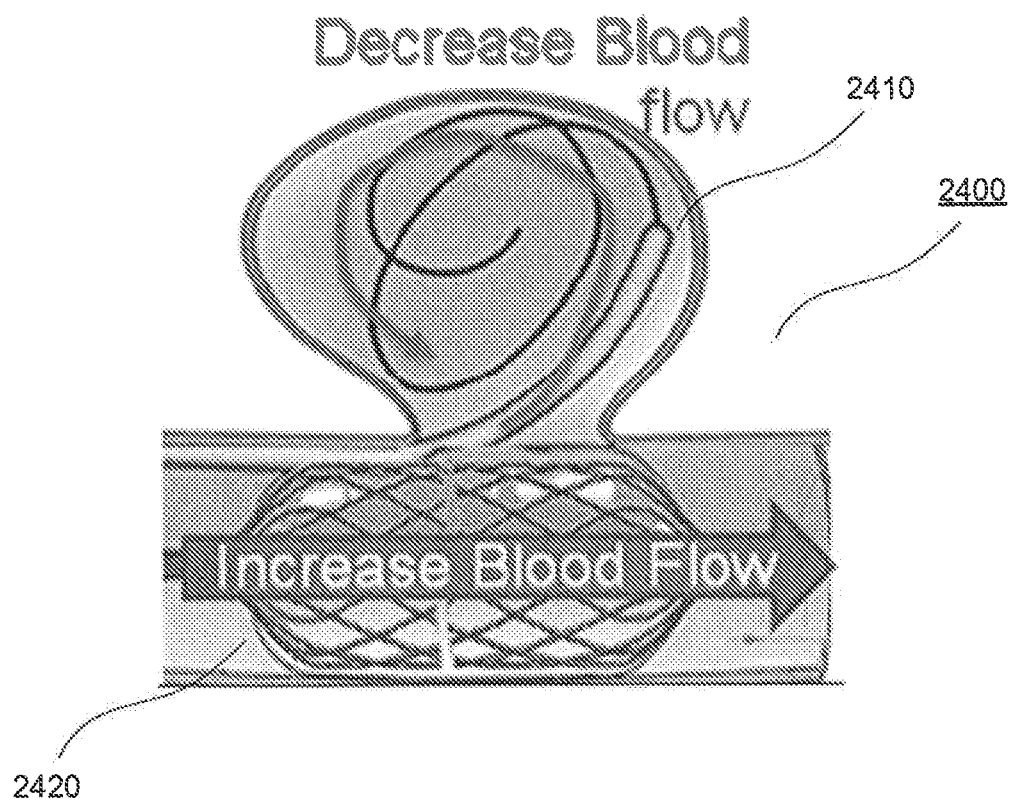
FIG. 24 is a perspective view of an embodiment consistent with the disclosure configured to divert blood flow away from an aneurysm.
Figure 25:
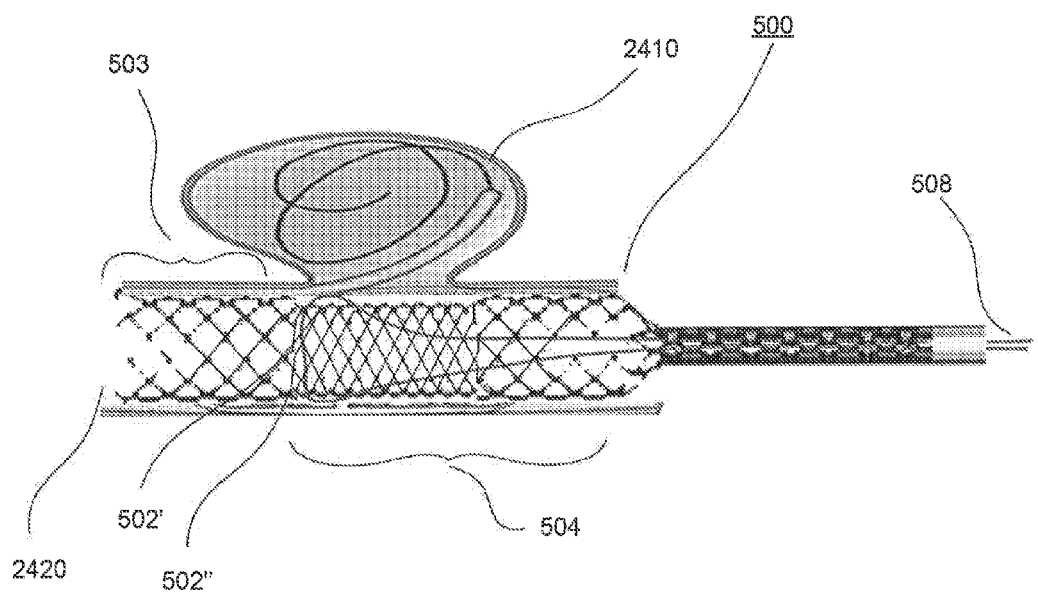
FIG. 25 is a perspective view of a further embodiment consistent with the disclosure configured to divert blood flow away from an aneurysm.

Moreover, consistent with this disclosure and depicted in FIGS. 24 and 25, a device 2400 (or the device 500) can be configured as a temporary blood flow diverter. Diverting blood flow from an aneurysm sac 2410 into a parent vessel 2420 can be beneficial during endovascular aneurysm treatment, because it can accelerate blood coagulation inside the aneurysm. In an embodiment, diversion of blood flow can be accomplished by providing pulling force at least one of the elongated control members in a manner than can decrease the size of the cells in the expandable member proximal to the aneurysm sac 2410. According to some embodiments the elongated control filaments can be manipulated to exhibit a greater density around the aneurysm neck and to exhibit less density otherwise. As a result, the device can block blood from flowing to the aneurysm and allow blood to continue flowing to vessel branching or perforating from the parent vessels. An embodiment consistent with this disclosure is illustrated in the FIG. 25, where controllable portion 503 is characterized by a certain filament density, and controllable portion 504 can exhibit a different filament density due to use of the control filaments associated with elongated control members. In addition, the filaments of the expandable member can be coated to prevent local thrombosis and further mitigate the use of anticoagulant drugs.

Figure 26A:
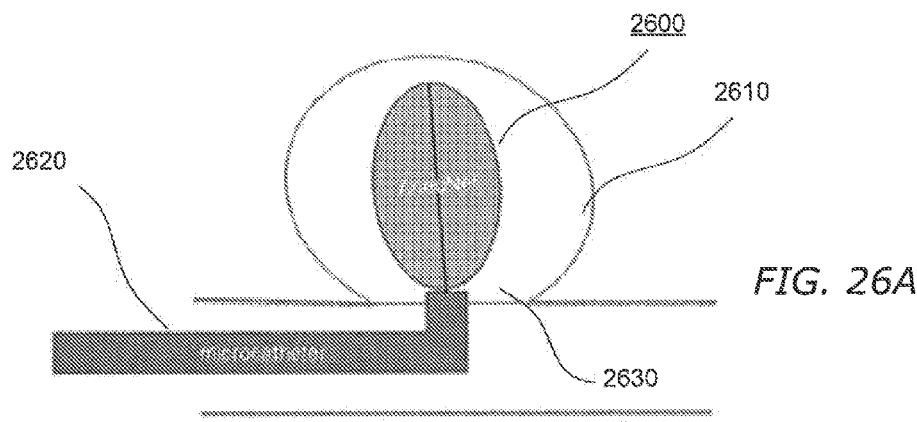
FIGS. 26A-C are perspective views illustrating aspects of a method of deploying a device consistent with the disclosure.
Figure 26B:
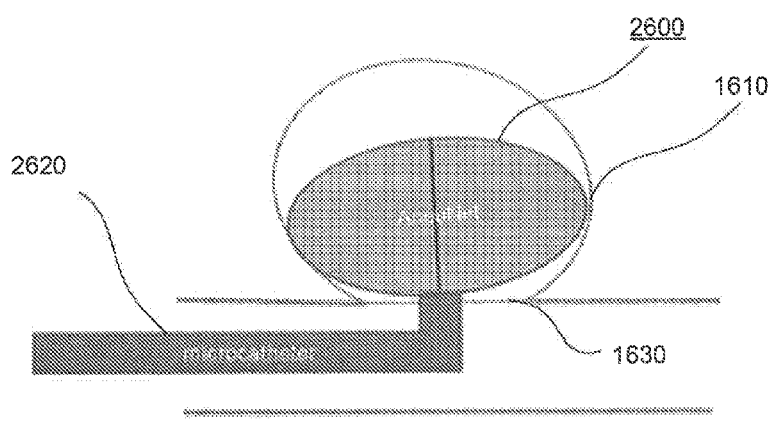
Figure 26C:
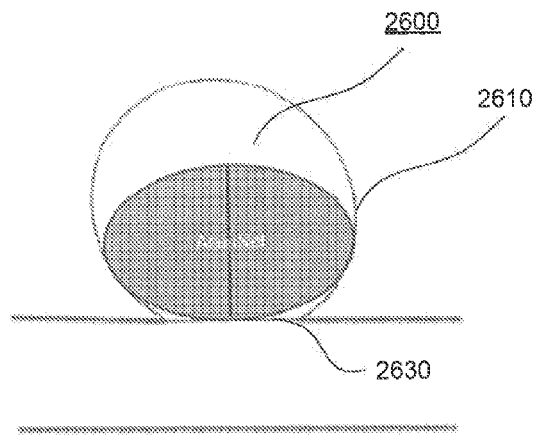

Consistent with the current disclosure, a device 2600 can also be configured to be deployed inside an aneurysm sac 2610, where the one or more control filaments can be utilized to optimize opposition inside the sac. This is depicted in FIGS. 26A-C. For example, in the same way that a detachable balloon can be deployed, the device 2600 can be unsheathed at the aneurysm 2610, and then expanded until an aneurysm neck 2630 is completely obstructed, and then the device 2600 can be detached (such as from a microcatheter 2620). This design does not require anticoagulation therapy (on the contrary it is dependent on coagulation to succeed) and one size of device 2600 can be configured to fit many dimensions of the aneurysm 2610, allowing the physician to make any final adjustment in-situ.

Embodiments of any of the devices described herein can be used during various endovascular procedures. During these procedures, the user can control the usable length of the expandable member, its outer diameter, its cell size and its filament density. Moreover, because more than one control filament can be used, a user can vary the above characteristics in various portions of the expandable device. Further still, because the expandable member can be delivered to a target vessel through a microcatheter (such as microcatheter 2620 depicted in FIG. 26A and FIG. 6B), its practical length can be controlled by partial unsheathing. The outer diameter and cell size can also be controlled via the one or more elongated control members.

Figure 27:
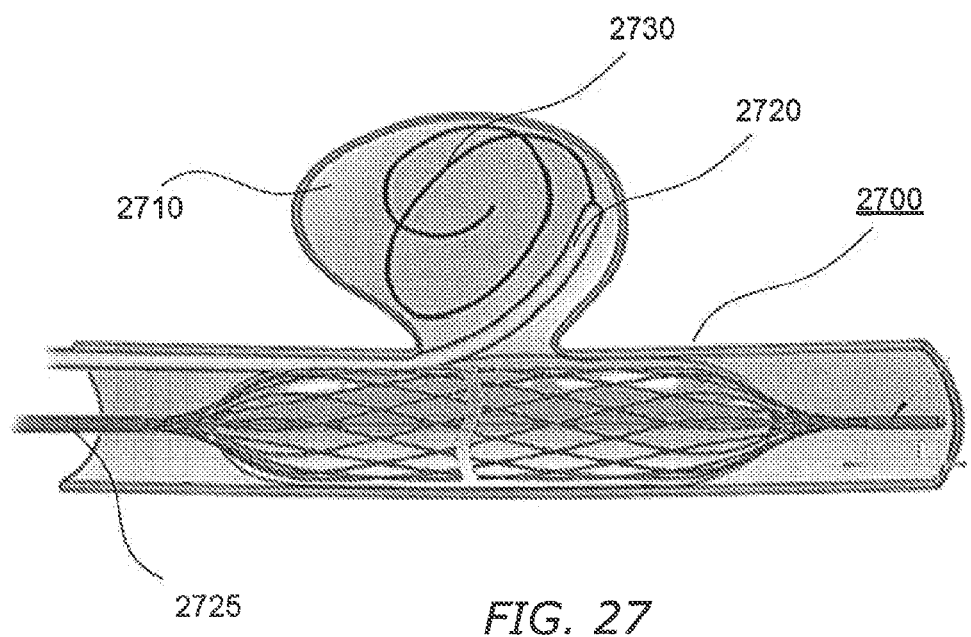
FIG. 27 is a perspective view depicting an embodiment consistent with the disclosure assisting intracranial aneurysm repair with coils.

Consistent with the disclosure herein, the device 2700 depicted in FIG. 27 can also be configured to support intracranial aneurysm repair with coils. A device operator can deliver two microcatheters to a target vessel, one microcatheter 2720 for delivering a coil 2730 (or coils) inside the aneurysm 2710 and the second microcatheter 2725 to deliver the device 2700. The coiling microcatheter 2720 can be normally placed inside the aneurysm 2710 and the device 2700 can be delivered and expanded in parallel to the coiling microcatheter 2720. This can cause the coiling microcatheter 2720 to be "jailed" inside the aneurysm 2710 and therefore provide a clinician with more control during the procedure. At the end of the procedure, the expandable member can be re-sheathed inside the microcatheter 2725 and then retrieved. The device 2700 can also be used during additional embolization techniques such as using liquids. Because the cell size adjacent to the aneurysm neck can be controlled with one or more control filaments, the cells can be adjusted to a size that is suitable for these alternative techniques. The device demonstrated in FIG. 25 can also be utilized for a similar purpose.

Embodiments of a treatment device consistent with the disclosure can also be used for endovascular treatment of vasospasm. Similar to a balloon that is expanded at the vessel suffering from vasospasm, the elongated control members (either individually or together) can be pulled to provide an available radial force on vessel walls (i.e., the elongated control members can be manipulated to exert the required radial force on the vessel). Because the device operator can have tactile feedback during the expansion of the device through the one or more elongated control members (e.g. control filaments) and visual feedback if the device is radio-opaque, the device operator can decide on the amount of force to apply during the procedure.

Figure 28:
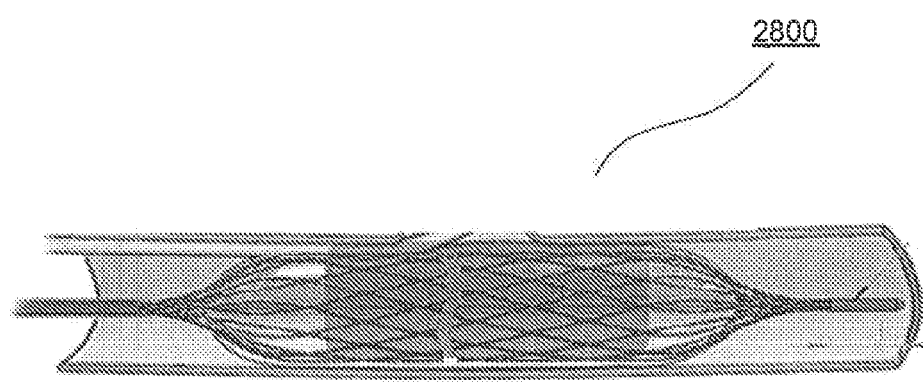
FIG. 28 is a perspective view depicting an embodiment consistent with the disclosure assisting a thrombectomy.

Furthermore, embodiments of a treatment device consistent with the disclosure can be used for thrombectomy. This embodiment is depicted in FIG. 28. In this case, it can be beneficial to control the amount of force exerted during the procedure combined with visual feedback on the actual dimensions of a device 2800 at the vessel. Device 2800 can be deployed adjacent or distally to the clot (similar to a "Stentriever") and then expanded as required. After deployment, the device 2800 can be retrieved in its expanded state. The physician can decide to expand the device 2800 even further during retrieval if the clot is pulled into vessels with a larger diameter.

Figure 29A:
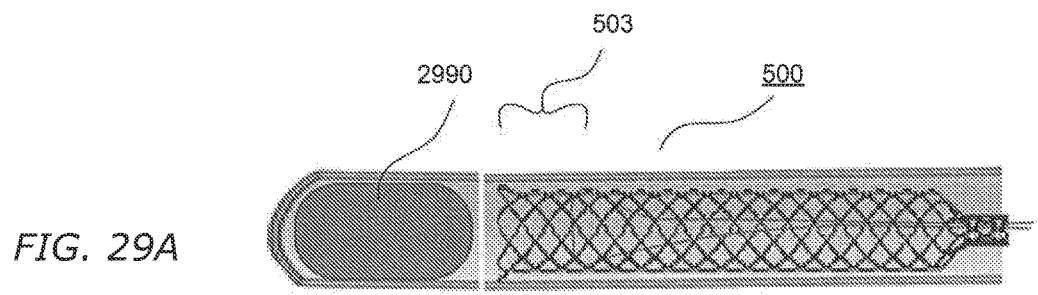
FIGS. 29A-D are perspective views of an embodiment consistent with the disclosure assisting a thrombectomy.
Figure 29B:
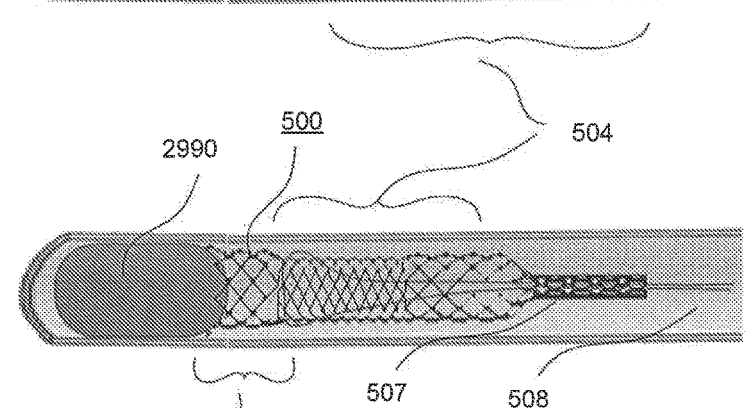
Figure 29C:
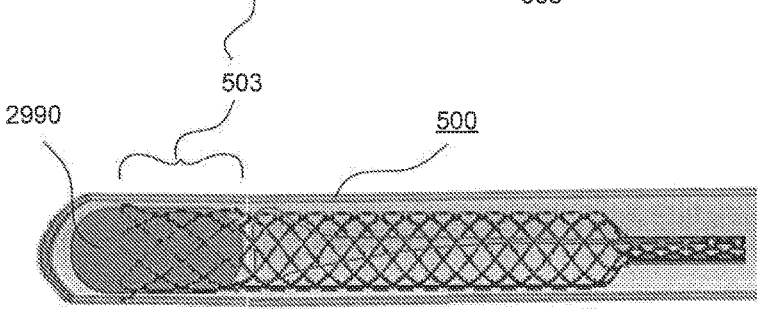
Figure 29D:
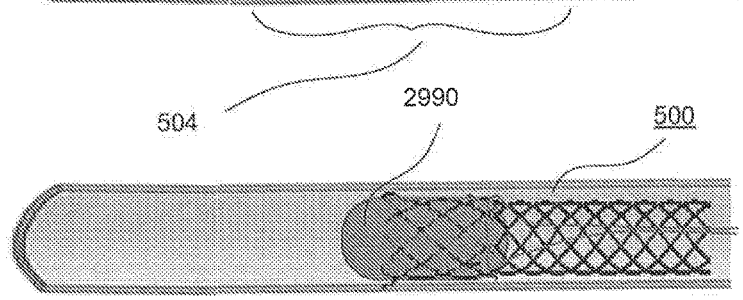

Furthermore, embodiments of a device consistent with the disclosure can be used for crossing a blocked blood vessel in a further manner. An exemplary procedure according to this embodiment is depicted in FIGS. 29A-D. In this case, device 500 has one or more elongated control members 508 at the distal end, and portions of the expandable member can be expanded to exhibit a substantially unobstructed channel and then pushed forward over a thrombus 2990. This maneuver can be repeated until the thrombus 2990 is partially or completely covered by the expandable member. In FIG. 29A, device 500 is shown before the control members undergo a pulling force in a proximal direction relative to the shaft, hence the filament density and the girth of the expendable member is substantially the same in controllable portion 503 as in controllable portion 504. As depicted in FIGS. 29A-D, controllable portion 503 is a portion of expandable member from the open end to a region where an elongated control member connects, interweaves, is knotted, and/or looped to the filament of the expandable member, and controllable portion 504 is a portion of expandable member from a region where the elongated control member connects, interweaves, is knotted, and/or looped to the filament of the expandable member to the distal end of the shaft 507. In FIG. 29B device 500 is shown after the elongated control member 508 undergoes a pulling three in a proximal direction relative to the shaft 507. Accordingly the filament density in controllable portion 504 has increased. After the elongated control member 508 undergoes a pulling force, device 500 can be brought close to thrombus 2990. In FIG. 29C the device is shown after undergoing a pushing three (in some embodiments it is not necessary to apply a pushing force to the control members, only to release the pulling force). As shown in the figure, part of controllable portion 503—which previously exhibited a substantially unobstructed channel—has covered the thrombus 2990. FIG. 29D shows device 500 after the thrombus is covered, and the device is retrieved in its expanded state. Because the device interacts with the thrombus or blockage from the proximal to the distal side this can beneficial in cases where the blockage cannot be crossed prior to retriever. In addition, because the expandable member can be configured to not over-expand the vessel the device can be manipulated in to exert minimal force on the vessel wall during the retrieval. According to some embodiments the usage described herein the device can be further utilized by attaching a motor or a vibrating source to the shaft to some or all the elongated one or more control members. According to another embodiment more than one motor (e.g. two motors or more) can be connected to the one or more control filaments or shaft to create more complex manipulations of the expandable member. Repeatedly vibrating or manipulating the expandable member can facilitate clot entrapment by the discussed device. As discussed earlier in connection with FIG. 5, additional elongated control filaments can be used in order to provide further control.

Further still, a device consistent with the disclosure can be used to expand other endovascular devices (such as stents). It can be utilized in a similar way the balloon is used, using the control filaments (such as the one or more elongate control members) to expand it when necessary and to retrieve at the end of the procedure.

It will be apparent to those skilled in the art that various modifications and variations can be made in the disclosed devices and methods without departing from the scope of the disclosure. That is, other embodiments will be apparent to those skilled in the art from consideration of the specification and practice of the embodiments disclosed therein, it is intended that the specification and embodiments be considered exemplary only, with a true scope of the invention being indicated by the following claims and their equivalents.

What is claimed:

1. A treatment device comprising:
   a shaft including a distal end;
   an expandable member including a proximal end and a distal end, wherein the proximal end of the expandable member is coupled to the distal end of the shaft; and
   a first elongated control member and a second elongated control member;
   wherein the expandable member further includes at least a first controllable portion and a second controllable portion;
   wherein the expandable member, including the first controllable portion and the second controllable portion, is configured to transition between at least a partially retracted configuration and an expanded configuration under control of at least the first elongated control member; and
   wherein the first controllable portion is configured to transition between at least a partially retracted configuration and an expanded configuration, while the second controllable portion is configured to remain substantially unchanged, under control of at least the second elongated control member.

2. The treatment device of claim 1, wherein the second controllable portion is distal and adjacent to the first controllable portion.

3. The treatment device of claim 2, further comprising a third controllable portion and a third elongated control member, wherein the first controllable portion is configured to transition between at least the partially retracted configuration and the expanded configuration while the third controllable portion is configured to remain substantially unchanged; and wherein the third controllable portion is proximal and adjacent to the first controllable portion.

4. The treatment device of claim 1, wherein the first elongated control member and the second elongated control member are configured to be controlled by at least one motor.

5. The treatment device of claim 1, wherein the first elongated control member is configured to partially retract the expandable member when the first elongated control member undergoes a pulling force in a proximal direction, and wherein the first elongated control member is configured to expand the expandable member when the first elongated control member undergoes a pushing force in a distal direction.

6. The treatment device of claim 1, wherein a distal end of at least one of the first elongated control member and the second elongated control member is configured to be substantially atraumatic to vessel walls.

7. The treatment device of claim 1, wherein the expandable member is configured to exhibit a substantially uniform shape between its proximal end and its distal end in an expanded configuration.

8. The treatment device of claim 1, wherein the expandable member is configured to exhibit a substantially asymmetrical shape between its proximal end and its distal end in an expanded configuration.

9. The treatment device of claim 1, wherein the expandable member is configured to exhibit at least two substantially uniform shapes between its proximal end and its distal end in an expanded configuration.

10. The treatment device of claim 9, wherein the at least two substantially uniform shapes comprise a pear-shape.

11. The treatment device of claim 1, wherein the expandable member is configured to exhibit at least a first substantially asymmetrical shape and at least one of; a substantially uniform shape and a second substantially asymmetrical shape, between its proximal end and its distal end in an expanded configuration.

12. The treatment device of claim 1, wherein the distal end of the expandable member includes an opening with a circumference value, the circumference value being-substantially equal to a girth of the expandable member in the expanded configuration.

13. The treatment device of claim 1, wherein the expandable member includes wire, and wherein the first elongated control member is configured as an extension of the wire of the expandable member.

14. The treatment device of claim 1, wherein the expandable member includes wire, wherein the first elongated control member includes control wire, and wherein the control wire is intertwined with the wire of the expandable member.

15. The treatment device of claim 14, wherein the control wire is looped through the wire of the expandable member.

16. The treatment device of claim 14, wherein the control wire is intertwined with a substantially distal portion of the expandable member.

17. The treatment device of claim 14, wherein the control wire is intertwined with a substantially middle portion of the expandable member.

18. The treatment device of claim 14, wherein the control wire is intertwined with a substantially proximal portion of the expandable member.

19. The treatment device of claim 1, wherein the expandable member includes wire, and wherein the wire of the expandable member is an extension of a portion of the shaft.

20. The treatment device of claim 1, wherein the expandable member includes wire, and wherein the wire of the expandable member exhibits a diameter between approximately 50 µm and approximately 120 µm.

21. The treatment device of claim 1, wherein the first elongated control member includes control wire, and wherein the control wire exhibits a diameter less than approximately 50 µm.

22. The treatment device of claim 1, wherein the expandable member includes material selected from at least one of a group of expandable materials, the group of expandable materials including: polymer material, metal, and metal alloy.

23. The treatment device of claim 1, wherein the expandable member includes Nitinol.

24. The treatment device of claim 1, wherein the expandable member includes a radio-opaque material.

25. The treatment device of claim 24, wherein the expandable member includes wire, wherein the radio-opaque material is a core of the wire, and wherein the radio-opaque material is between approximately 20 percent to approximately 50 percent of the wire by volume.

26. A method of treatment comprising the steps of:
deploying a treatment device into a blood vessel, the treatment device including a shaft having a distal end and the treatment device including an expandable member coupled to the distal end of the shaft, the expandable member including a first controllable portion and a second controllable portion;
transitioning the expandable member from at least a partially retracted configuration to an expanded configuration by exerting a force on a first elongated control member in a first direction, the first direction selected from a group of directions including: a proximal direction and a distal direction; and
transitioning the first controllable portion of the expandable member from at least an expanded configuration to a partially retracted configuration, while keeping the second controllable portion substantially unchanged, by exerting a force on a second elongated control member in a second direction, the second direction selected from the group of directions.

27. The method of claim 26, wherein the first elongated control member is connected to a distal end of the expandable member, and wherein the direction selected from a group of directions is the proximal direction.

28. The method of claim 26, wherein a wire density of the first controllable portion of the expandable member is configured to be controllably varied under control of at least the second elongated control member.

* * * * *